(12) United States Patent
Thottathil et al.

(10) Patent No.: US 9,434,740 B2
(45) Date of Patent: *Sep. 6, 2016

(54) TAXANE COMPOUNDS, COMPOSITIONS AND METHODS

(71) Applicant: GFV, LLC, San Diego, CA (US)

(72) Inventors: John K. Thottathil, Mudelein, IL (US); Raymond P. Warrell, Westfield, NJ (US)

(73) Assignee: ODONATE THERAPEUTICS, LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/325,960

(22) Filed: Jul. 8, 2014

(65) Prior Publication Data

US 2015/0080578 A1    Mar. 19, 2015

Related U.S. Application Data

(63) Continuation of application No. 13/170,830, filed on Jun. 28, 2011, now Pat. No. 8,785,669.

(60) Provisional application No. 61/360,135, filed on Jun. 30, 2010.

(51) Int. Cl.
| | |
|---|---|
| *C07D 493/08* | (2006.01) |
| *C07D 205/08* | (2006.01) |
| *C07D 305/14* | (2006.01) |
| *C07D 407/02* | (2006.01) |
| *C07D 401/04* | (2006.01) |

(52) U.S. Cl.
CPC .......... *C07D 493/08* (2013.01); *C07D 205/08* (2013.01); *C07D 305/14* (2013.01); *C07D 401/04* (2013.01); *C07D 407/02* (2013.01)

(58) Field of Classification Search
CPC .......................... C07D 317/70; C07D 493/02
USPC .................................................. 549/432, 510
See application file for complete search history.

(56) References Cited

U.S. PATENT DOCUMENTS

| | | |
|---|---|---|
| 6,075,140 A | 6/2000 | Terasawa et al. |
| 6,211,363 B1 | 4/2001 | Terasawa et al. |
| 6,310,201 B1 | 10/2001 | Thottathil et al. |
| 6,350,887 B1 | 2/2002 | Thottathil et al. |
| 6,646,123 B2 | 11/2003 | Terasawa et al. |
| 6,677,456 B2 | 1/2004 | Soga et al. |
| 6,730,782 B2 | 5/2004 | Holton et al. |
| 6,794,523 B2 | 9/2004 | Holton et al. |
| 7,126,003 B2 | 10/2006 | Sato et al. |
| 7,176,326 B2 | 2/2007 | Thottathil et al. |
| 7,410,980 B2 | 8/2008 | Uchida et al. |
| 7,456,302 B2 | 11/2008 | Imura et al. |
| 7,678,919 B2 | 3/2010 | Imura et al. |
| 8,785,669 B2 * | 7/2014 | Thottathil et al. ............ 549/510 |
| 2002/0091274 A1 | 7/2002 | Holton et al. |

FOREIGN PATENT DOCUMENTS

| | | | |
|---|---|---|---|
| EP | 1942109 A1 | 7/2008 | |
| EP | 1942109 A1 * | 7/2008 | .................... 549/510 |
| JP | 2000159757 A | 6/2000 | |
| WO | 9633998 A1 | 10/1996 | |
| WO | 0127115 A1 | 4/2001 | |
| WO | 2005105807 A1 | 11/2005 | |
| WO | 2007049575 A1 | 5/2007 | |
| WO | 2013162922 A1 | 10/2013 | |

OTHER PUBLICATIONS

Takeda, Y. et al., "A New Method for Synthesis of 7-Deoxytaxane; Analogues by Hydrogenation of 6.7-Taxane Derivatives", *Chem. Pharm. Bull.*, 50(10)XP-0002655474, 1398-1400 (2002).
International Search Report and Written Opinion in PCT/US2011/042299 mailed Aug. 16, 2011.

* cited by examiner

*Primary Examiner* — Taofiq A. Solola
(74) *Attorney, Agent, or Firm* — Foley Hoag LLP; David P. Halstead

(57) ABSTRACT

The present invention provides a method for the preparation of orally available pentacyclic taxane compounds, as well as intermediates useful in their preparation.

12 Claims, 6 Drawing Sheets

TAXANE COMPOUNDS, COMPOSITIONS AND METHODS

CROSS-REFERENCE TO RELATED APPLICATIONS

This application is a continuation of U.S. application Ser. No. 13/170,830, filed Jun. 28, 2011, which claims the benefit of priority to U.S. Provisional Patent Application No. 61/360,135, filed Jun. 30, 2010. All the teachings of the above-referenced applications are incorporated herein by reference.

FIELD OF THE INVENTION

The present invention relates generally to methods for preparation of taxane derivatives that have antitumor activity and can be orally administered, in particular pentacyclic taxanes.

BACKGROUND OF THE INVENTION

Taxol is a natural substance represented by the following chemical structural formula, which can be obtained in small amounts from the bark or other parts of *Taxus brevifolia*.

It is known that taxol has antitumor activity, and its mechanism of action is believed to be based on its ability to inhibit depolymerization of microtubules during cell division. At the time of the discovery of taxol this mechanism of action was different from the conventional antitumor agents, so it became of great interest for its potential clinical application as an antitumor agent.

Taxol can be obtained from natural sources, but only in very small amounts. However, taxol derivatives can now be synthesized using a taxol precursor, 10-O-deacetylbaccatine III ("10-DAB III"), which can be obtained from leaves and other parts of *Taxus* plants in relatively larger amounts. One such taxol derivative, docetaxel, is marketed by Sanofi Aventis under the tradename Taxotere® and has been approved for the treatment of various cancers, including breast cancer.

Recently, in U.S. Pat. No. 6,646,123, inventors at Daiichi Pharmaceutical Co. reported on a series of pentacyclic taxane compounds. These pentacyclic taxanes were obtained by reduction of the 9-position ketone of known taxanes to form a 9-position hydroxyl group which was then linked to the 10-position hydroxyl group to form a cyclic acetal. The resulting compounds have strong antitumor activity.

Additional studies on pentacyclic taxanes are reported in U.S. Pat. No. 6,677,456 (Daiichi Sankyo). These compounds have oral antitumor activity and therefore the potential to eliminate the toxic side effects associated with the use of Cremophor EL (a polyoxyethylated castor oil) and polysorbate 80 to solubilize taxanes for intravenous administration. One such compound is tesetaxel, having the following structure.

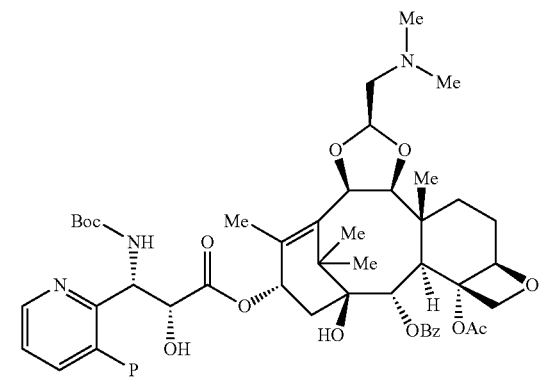

There is a continuing need for efficient and cost-effective synthesis schemes for preparing orally available taxol derivatives, such as tesetaxel, and for intermediates useful in such syntheses.

SUMMARY OF THE INVENTION

Accordingly, one aspect of the present invention is directed to a compound represented by formula (Ia) and methods for preparing a taxane, including tesetaxel, comprising reacting the compound represented by formula (Ia)

formula (Ia)

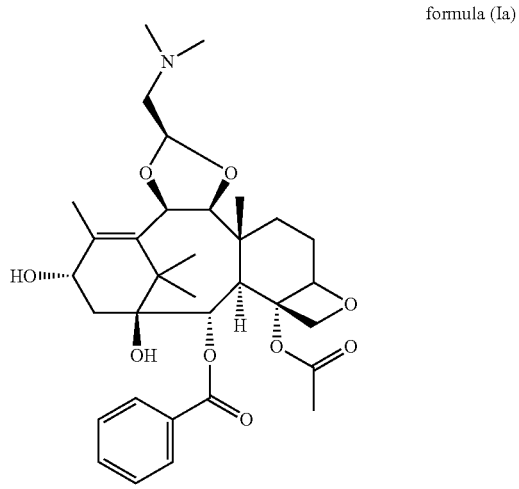

with a taxane side chain precursor compound to couple the side chain precursor compound to C13 of the compound represented by formula (Ia)

In a specific example, C13 of the compound represented by formula (Ia) is coupled with a side chain precursor compound represented by formula (II)

formula (II)

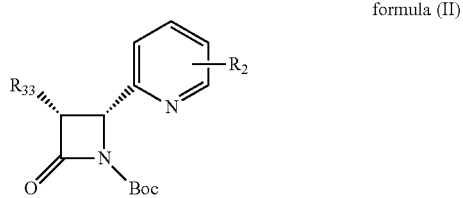

wherein $R^2$ is an alkoxy group having from 1 to 6 carbon atoms or a halogen atom such as fluorine (F), bromine (Br), iodine (I) or chlorine (Cl) and $R^{33}$ is a protected hydroxyl group.

For synthesis of pentacyclic taxanes other than tesetaxel, the dimethylaminomethyl group of the compound represented by formula (Ia) is replaced with any of the R4 and R5 substituents disclosed in U.S. Pat. No. 6,646,123, discussed above. In a specific embodiment the dimethylaminomethyl group is replaced with another amino-containing group such as morpholinomethyl.

In some embodiments, $R^{33}$ is triisopropylsilyl, while in others $R^{33}$ is methoxy methylethoxy (also referred to as 2-methoxy propyloxy or MOP).

According to another aspect of the invention, the compound represented by formula (Ib) is provided. In one embodiment, the compound represented by formula (Ia) can be derived from the precursor compound represented by formula (Ib)

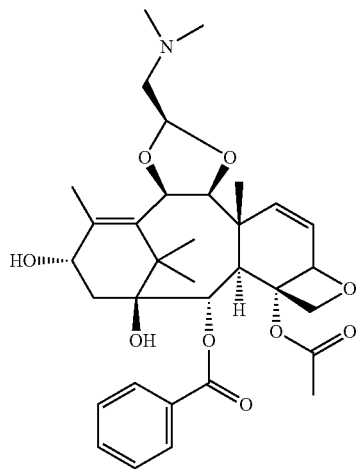

formula (Ib)

by reducing the C6-C7 double bond to a single bond.

Alternatively, the compound represented by formula (Ia) can be derived from a precursor compound represented by formula (III)

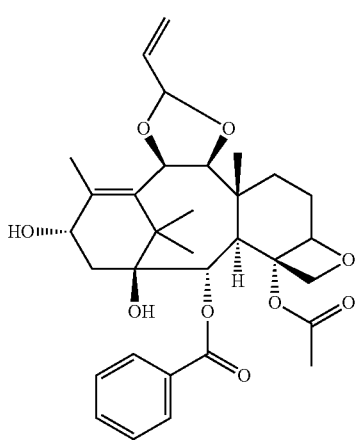

formula (III)

by converting the terminal olefin (vinyl) group to an aldehyde and reacting the product aldehyde with an amine to form a dimethylaminomethyl group.

Yet another aspect of the present invention provides a compound represented by formula (VII) which is useful as an intermediate compound in the synthesis of tesetaxel and other pentacyclic taxanes:

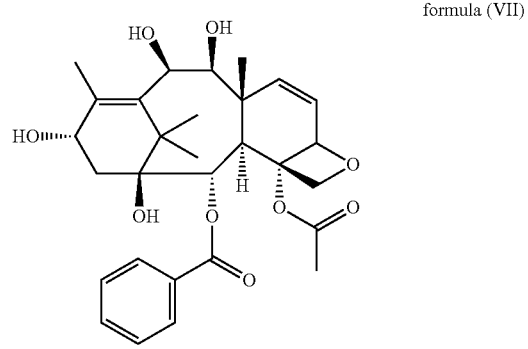

formula (VII)

The compounds represented by formulas (Ia), (Ib), (III) and (IV) are all derivable from the compound represented by formula (VII) according to the methods described herein.

Yet another aspect of the present invention provides a method for the preparation of DOH which involves reduction of the C6-C7 double bond of the compound represented by formula (VII) to obtain DOH.

Yet another aspect of the present invention provides a compound represented by formula (IX) which is useful as an intermediate compound in the synthesis of tesetaxel and other pentacyclic taxanes:

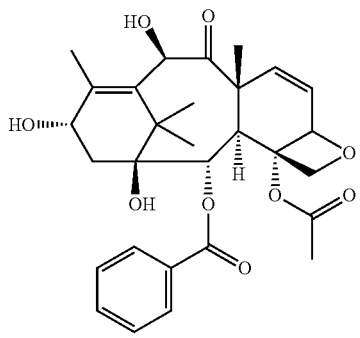

formula (IX)

The intermediate compounds represented by formulas (VII) and (XI) are derivable from the compound represented by formula (IX) as described herein.

Yet another aspect of the invention provides compound represented by formula (X) which is useful as an intermediate compound in the synthesis of tesetaxel and other pentacyclic taxanes:

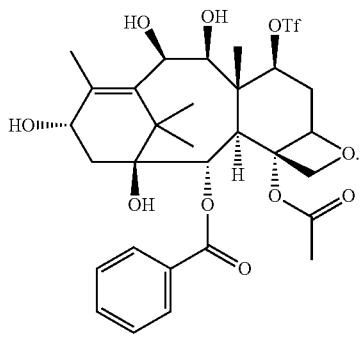

formula (X)

The intermediate compounds represented by formulas (VII), (Ib) and (Ia) are all derivable from the compound represented by formula (X) as described herein.

Another aspect of the present invention is directed to a compounds represented by formula (XI) which is useful as an intermediate compound in the synthesis of tesetaxel and other pentacyclic taxanes:

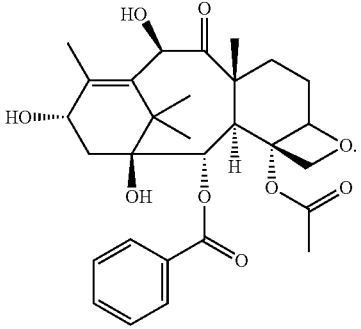

formula (XI)

The compound represented by formula (XI) can be derived from the compound represented by formula (IX) as described herein.

Another aspect of the present invention is directed to pharmaceutically acceptable acid addition salts of tesetaxel, including, for example, monobasic, dibasic or tribasic acid salts.

The compounds and methods employed in the syntheses of the invention provide several advantages and improvements over prior art compounds and methods for synthesis of Pentacyclic taxanes. First, active taxanes require handling and processing in high containment facilities due to their potency and toxicity. Such specialized handling substantially increases the cost of manufacture. The synthesis methods of the invention decrease the amount of time and handling under high containment conditions by making attachment of the side chain the last key synthetic step of the method. As taxanes become active only when the side chain is attached, in the inventive process special handling is only required for attachment of the side chain and purification of the final product. This substantially reduces the cost of taxane manufacture.

In addition, by making coupling of the well-characterized, purified, specification-set side chain to the well-characterized, purified, specification-set pentacyclic core intermediate the last key step of the synthesis a well characterized, highly purified specification-set product can be obtained reproducibly with better yield.

DETAILED DESCRIPTION OF THE INVENTION

Figure 1:
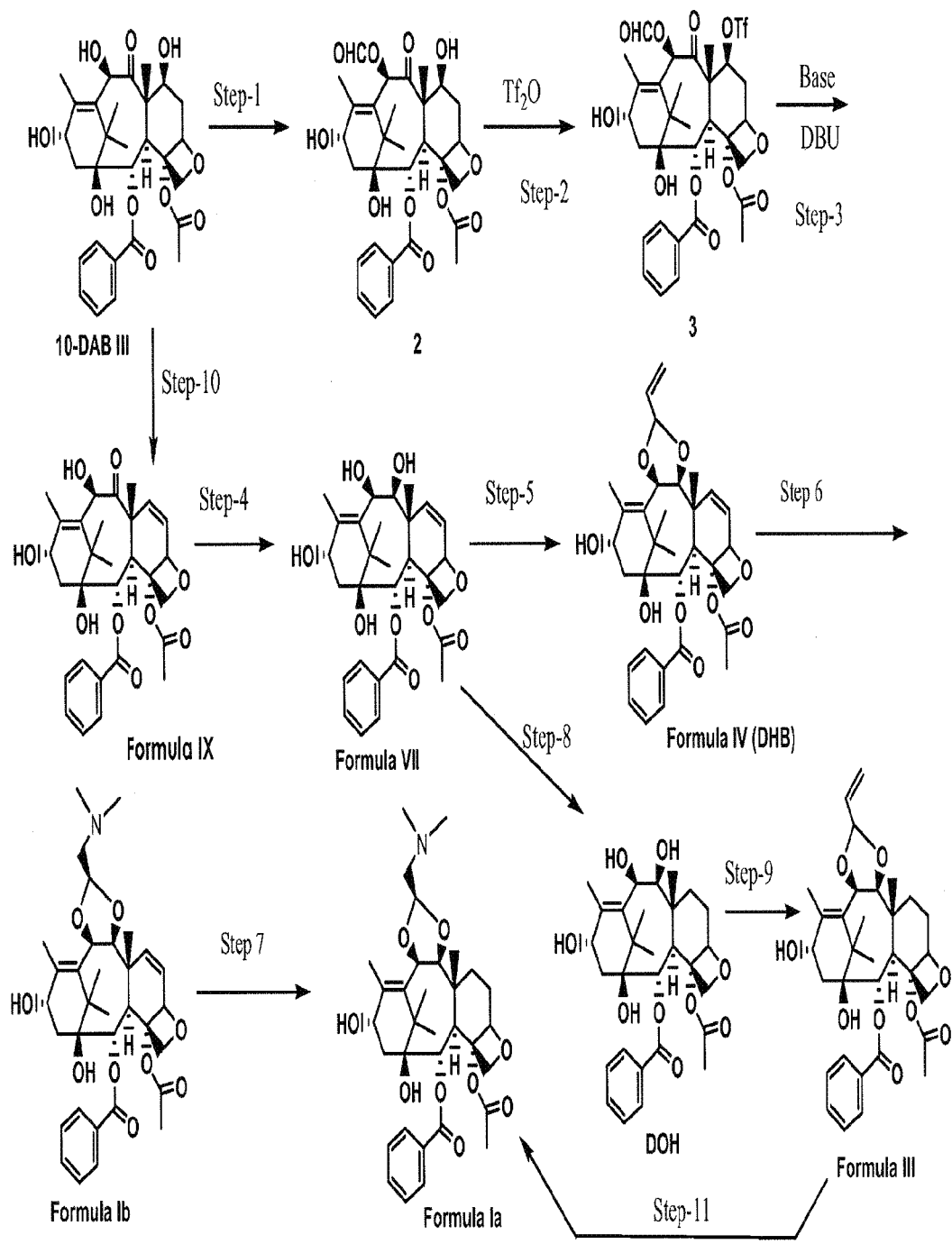
FIG. 1 is an illustration of a reaction scheme for synthesis of a pentacyclic taxane core structure, including alternative steps for synthesis of intermediates.

Although the invention herein is described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

As used herein, the designation "Me" means methyl, the designation "Bz" means benzoyl, the designation "Ac" means acetyl and the designation "Boc" means t-butoxycarbonyl.

As used herein, the term "derived" or "derivable" in connection with synthesis of a compound from a precursor compound means that the compound can be obtained by chemical synthesis from the identified precursor, either directly in a single step or in a multi-step process starting with the identified precursor compound.

One aspect of the present invention is directed to a method for the preparation of tesetaxel. In U.S. Pat. No. 6,677,456, tesetaxel is prepared by coupling the side chain to C13 of a polycyclic taxane core compound before completing synthesis of the tesetaxel fifth ring.

Applicants have found that a robust synthesis of pentacyclic taxane compounds having a dimethylaminomethyl or other amino-containing group in the fifth ring can be achieved by converting the vinyl group of the fifth ring precursor to the dimethylaminomethyl or other amino-containing group prior to attachment of a taxane side chain precursor to the 13-OH-position. In either of the schemes in U.S. Pat. No. 6,677,456, this means that the β-lactam intermediate is coupled to the 13-OH-position of the completed pentacyclic taxane core. These methods reduce the complexity and cost of synthesis of these toxic compounds and result in a higher yield of final product. Accordingly, methods for the preparation of tesetaxel and other pentacyclic taxanes incorporating the novel compounds represented by formulas (Ia), (Ib), (III), (VII), (IX), (X) and (XI) are provided.

The method for synthesis of a taxane compound comprises coupling a taxane side chain precursor compound to the C13 hydroxyl group of the compound represented by formula (Ia)

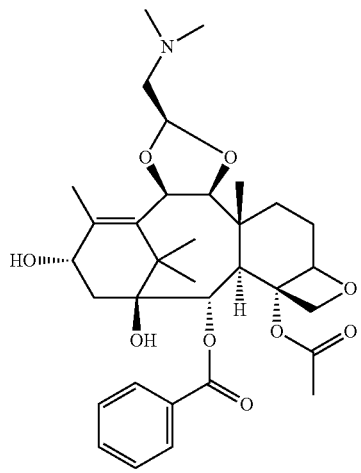

formula (Ia)

to produce a protected taxane reaction product, deprotecting the protected taxane reaction product, and isolating the taxane compound.

In a specific example, a taxane side chain precursor compound represented by formula (II):

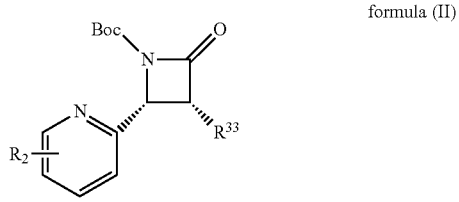

formula (II)

wherein $R^2$ is an alkoxy group having from 1-6 carbon atoms or a halogen atom and $R^{33}$ is a protected hydroxyl group, is coupled to the C13 hydroxyl of the compound represented by formula (Ia). A preferred $R^2$ substituent is fluorine at the 3-position of pyridine.

Compounds represented by formula (II) can be prepared by methods known in the art as well as the inventive methods described herein. For example, where R33 is triisopropylsilyl, the compound can be prepared using the method described in Example 13 of U.S. Pat. No. 6,677,456 and in U.S. Pat. No. 7,126,003 B2.

Other pentacyclic taxanes according to the invention can be synthesized by reacting a compound having a desired amino-containing group in place of the dimethylaminomethyl group of the compound represented by formula (Ia) with a compound having a desired pyridine or pyridine derivative in place of the fluoropyridine group of the compound represented by formula (II). In one such compound, the dimethylaminomethyl group of formula (Ia) is replaced by morpholinomethyl. For example, $R^2$ of formula (II) may be an alkoxy group having from 1 to 6 carbon atoms or an alternative halogen atom such as chlorine.

The compound represented by formula (Ia) can be derived from either the compound represented by formula (III):

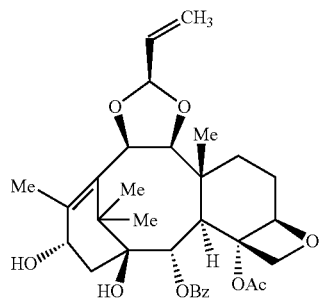

formula (III)

or the compound represented by formula (IV):

formula (IV)

using the relevant portions of Synthetic Method 1 or Synthetic Method 2, respectively, in U.S. Pat. No. 6,677,456. These methods include oxidation of the terminal double bond (i.e., the olefin) to remove one carbon and produce an aldehyde. The aldehyde is reductively aminated with dimethylamine with hydrogenation as necessary.

The compound represented by formula (Ia) may be prepared by converting the terminal olefin group of the cyclic acetal of the compound represented by formula (III) or formula (IV) to a diol group, for example using an alkali metal permanganate or osmium tetroxide. The diol is oxidatively cleaved to an aldehyde (e.g., using periodate) and converted to a dimethylaminomethyl group. These reactions are taught in connection with different intermediate compounds in U.S. Pat. No. 7,456,302 or U.S. Pat. No. 6,677,456, both of which are hereby incorporated by reference in their entirety. If the starting compound for this reaction is the compound represented by formula (IV), the product of the above reaction is the compound represented by formula (Ib) and the C6-C7 double bond is subsequently reduced to provide the compound represented by formula (Ia).

The cyclic acetal ring of the compounds represented by formulas (III) and (IV) can be formed using the same or similar methodology as described in connection with different intermediate compounds in U.S. Pat. No. 6,646,123, hereby incorporated by reference in its entirety. The method includes the use of acrolein dialkyl acetals (such as acrolein dimethyl acetal, acrolein diethyl acetal) with an acid catalyst (for example, camphorsulfonic acid) and, optionally, triethylamine, or with a Lewis acid catalyst (for example, zinc chloride).

The invention provides an alternative method for synthesis of the pentacyclic core of tesetaxel (i.e., the compound represented by formula Ia) which is more economical and practical than methods of the prior art. It will also be appreciated by one of skill in the art that the synthesis methods of the invention can be adapted to produce the core structures of other pentacyclic taxanes. Included in the reactions of the invention are syntheses for the novel intermediates represented by formula (Ia), formula (Ib), formula (III), formula (VII), formula (IX), formula (X) and formula (XI).

The method of making a taxane compound according to the invention comprises coupling a taxane side chain precursor compound to the C13-hydroxyl of the compound represented by formula (Ia) to produce a protected taxane, reaction product, deprotecting the protected taxane reaction product, and isolating the taxane compound. A specific example of a reaction scheme for synthesis of the pentacyclic tesetaxel core (i.e., the compound represented by formula (Ia)) is illustrated in FIG. 1.

Referring to FIG. 1, in a first aspect the compound represented by formula (Ia) can be synthesized according to Steps 1-7, starting with 10-DAB III. In this embodiment, the compound represented by formula (Ia) is derived from the compound represented by formula (Ib), which is derived from the compound represented by formula (VII), which is derived from the compound represented by formula (IX):

Step-1: Formylation of C10 of 10-DAB III. (e.g., using $Tf_2O$/DMAP/DMF);

Step-2: Triflic anhydride reaction of the C7 hydroxyl. (e.g., using $Tf_2O$/Pyridine/$CH_2Cl_2$);

Step-3: Formation of a C6-7 double bond and hydrolysis of the C10 formyl ester to produce the compound represented by formula (IX). (e.g., a. Base such as $Me_2NH$/THF, b. Base such as DBU/THF);

Step-4: Reduction of the C9 ketone to form a diol compound having hydroxyls at C9 and C10, producing the compound represented by formula (VII). (e.g., hydride reduction such as $BH_3$, $NaBH_4$ or $(Bu)_4NBH_4$);

Step-5: Formation of a C9-C10 cyclic acetal attached to a terminal olefin group, producing DHB. (acroline acetal and acid catalyst (e.g., camphor sulfonic acid, TFA or TSA) or Lewis acid (e.g., anhydrous zinc chloride));

Step-6: Oxidative cleavage of the terminal olefin group of the cyclic acetal to form an aldehyde, and reductive amination of the aldehyde, producing the compound represented by formula (Ib). (a. conversion of olefin to diol, e.g., $KMnO_4$ or $OsO_4$, b. oxidative cleavage of the diol to an aldehyde, e.g., periodate, e.g., $NaIO_4$, c. conversion of the aldehyde to a dimethylaminomethyl group, e.g., $Me_2NH$/AcONa/$NaBH(OAc)_3$); and Step-7: Hydrogenation of the C6-7 double bond to produce the compound represented by formula (Ia). (e.g., Rh—Al2O3/$H_2$, Pd—C/$H_2$ or Pd—C/$HCOONH_4$).

Again referring to FIG. 1, in an alternative route for synthesis of the compound represented by formula (Ia), the reaction proceeds as described above from Steps 1-4. In this embodiment, the compound represented by formula (Ia) is derived from the compound represented by formula (III), which is derived from the compound represented by formula (VII), which is derived from the compound represented by formula (IX). Following Step 4, the synthesis proceeds as follows to produce the compound represented by formula (III):

Step-8: Hydrogenation of the C6-7 double bond of the diol compound represented by formula (VII) to produce DOH. (e.g., Rh—$Al_2O_3$/$H_2$ or Pd—C/$H_2$ or Pd—C/$HCOONH_4$);

Step-9: Formation of a C9-C10 cyclic acetal attached to a terminal olefin group, producing the compound represented by formula (III). (e.g., acroline acetal/CSA (camphor sulfonic acid) or other acid catalyst (for example, TFA or TSA or Lewis acids such as anhydrous zinc chloride)).

The compound represented by formula III is then converted directly to the compound represented by formula (Ia) by oxidative cleavage of the terminal olefin group to form an aldehyde and reductive amination of the aldehyde. (a. conversion of olefin to diol, e.g., $KMnO_4$ or $OsO_4$, b. oxidative cleavage of the diol to aldehyde, e.g., periodate, e.g., $NaIO_4$, c. conversion of aldehyde to a dimethylaminomethyl group, e.g., $Me_2NH$/AcONa/$NaBH(OAc)_3$) as shown in Step 11 of FIG. 1.

Further alternative syntheses provided by the invention for producing the compound represented by formula (Ia) include alternative methods for deriving the compound represented by formula (IX) (the precursor of the compound represented by formula (VII) from 10-DAB III. In a first alternative reaction scheme illustrated as Step 10 in FIG. 11, and as Step 1 and Step 2 in FIG. 4, 10-DAB III is converted to the compound represented by formula (IX) by formation of a C6-C7 double bond. The double bond may be formed, for example, by reaction of the C7 hydroxyl of 10-DAB III with triflic anhydride (e.g., $Tf_2O$/Pyridine/$CH_2Cl_2$) followed by base such as (DBU)/THF) to form the C6-C7 double bond of the compound represented by formula (IX). The reaction then proceeds through Steps 4-7 of FIG. 1 as described above to obtain the compound represented by formula (Ia). Alternatively, the reaction steps can proceed through Step 4, Step 8, Step 9 and Step 11 of FIG. 1 as previously described.

Figure 3:
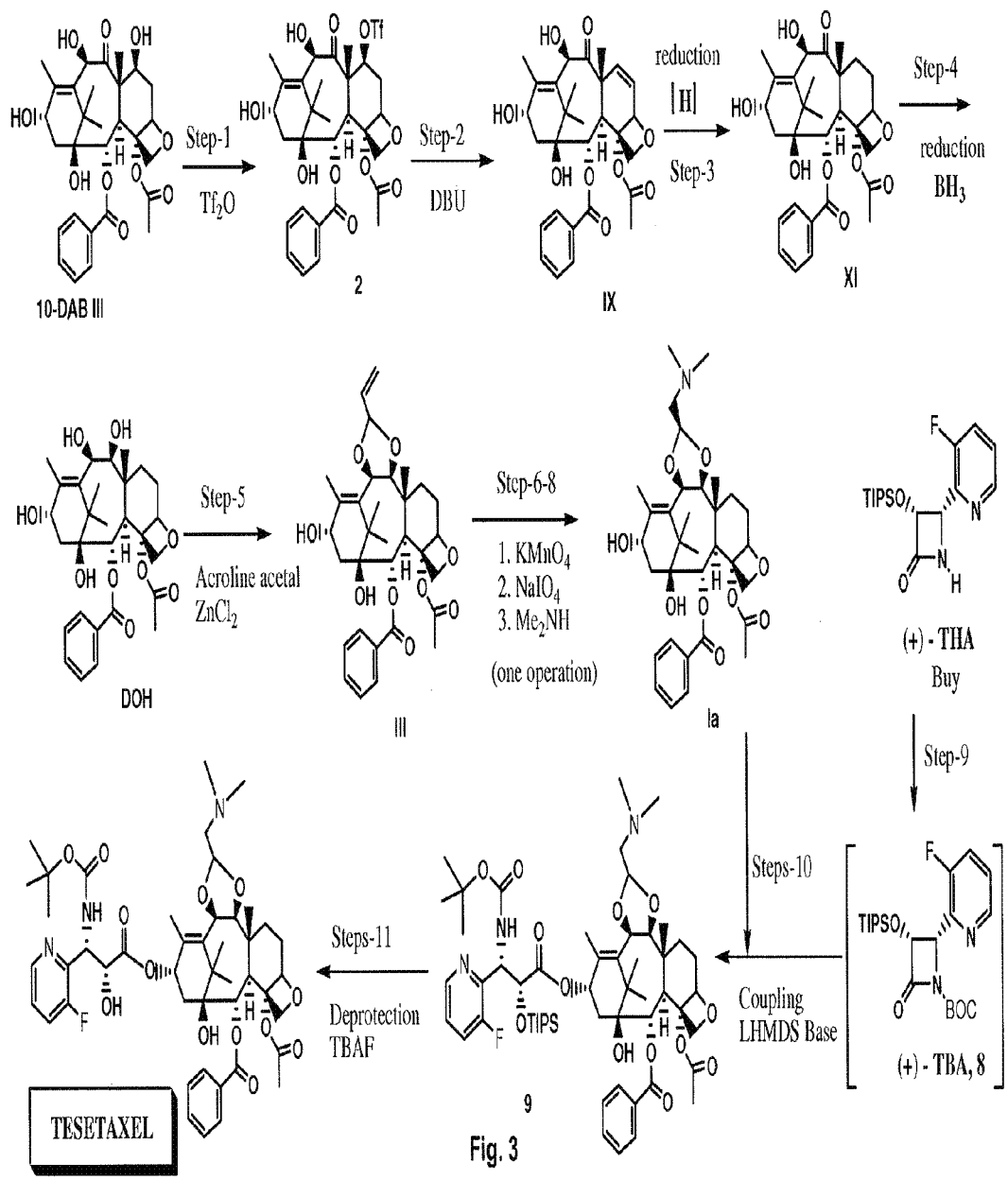
FIG. 3 is an illustration of a specific reaction scheme for synthesis of the compound represented by formula (Ia) and conversion of formula (Ia) to tesetaxel.

Referring to FIG. 3, an alternative reaction scheme for synthesis of a pentacyclic taxane is illustrated using tesetaxel as an example. This synthesis does not involve the C10 formyl ester intermediate of FIG. 1. In this alternative aspect of the invention the compound represented by formula (Ia) is derived from the compound represented by formula (III), which is derived from the compound represented by formula (IX). The compound represented by formula (Ia) can be synthesized according to Steps 1-8 of FIG. 3, starting with 10-DAB III:

Step 1: Reaction of the C7 hydroxyl of 10-DAB III with triflic anhydride. (e.g., $Tf_2O$/Pyridine/$CH_2Cl_2$);

Step 2: Formation of a C6-7 double bond by base elimination to form the compound represented by formula IX. (e.g., DBU);

Step 3: Reduction of the C6-7 double bond by hydrogenation of compound 1X to produce the compound represented by formula (XI). (e.g., with Rh—$Al_2O_3$/$H_2$ or Pd—C/$H_2$ or Pd—C/$HCOONH_4$);

Step 4: Reduction of the C9 ketone to produce a diol compound having hydroxyls at C9 and 010 (DOH). (e.g., using $BH_3$, $NaBH_4$ or $(Bu)_4NBH_4$);

Step 5: Formation of a C9-C10 cyclic acetal from the diol DOH to produce the compound represented by formula (III), wherein the cyclic acetal is attached to a terminal olefin group. (acroline acetal and acid catalyst (e.g., camphor sulfonic acid, TFA or TSA) or Lewis acid (e.g., anhydrous zinc chloride)); and Steps 6-8: Oxidative cleavage of the terminal olefin group to an aldehyde and reductive amination of the aldehyde to produce the compound represented by formula (Ia). (a. conversion of olefin to diol, e.g., $KMnO_4$ or $OsO_4$, b. oxidative cleavage of the diol to the aldehyde, e.g., periodate, e.g., $NaIO_4$, c. conversion of aldehyde to a dimethylaminomethyl group, e.g., $Me_2NH$/AcONa/

NaBH(OAc)₃). The reactions of Steps 6-8 can be accomplished in a single operation without any purification of intermediates.

Figure 4:
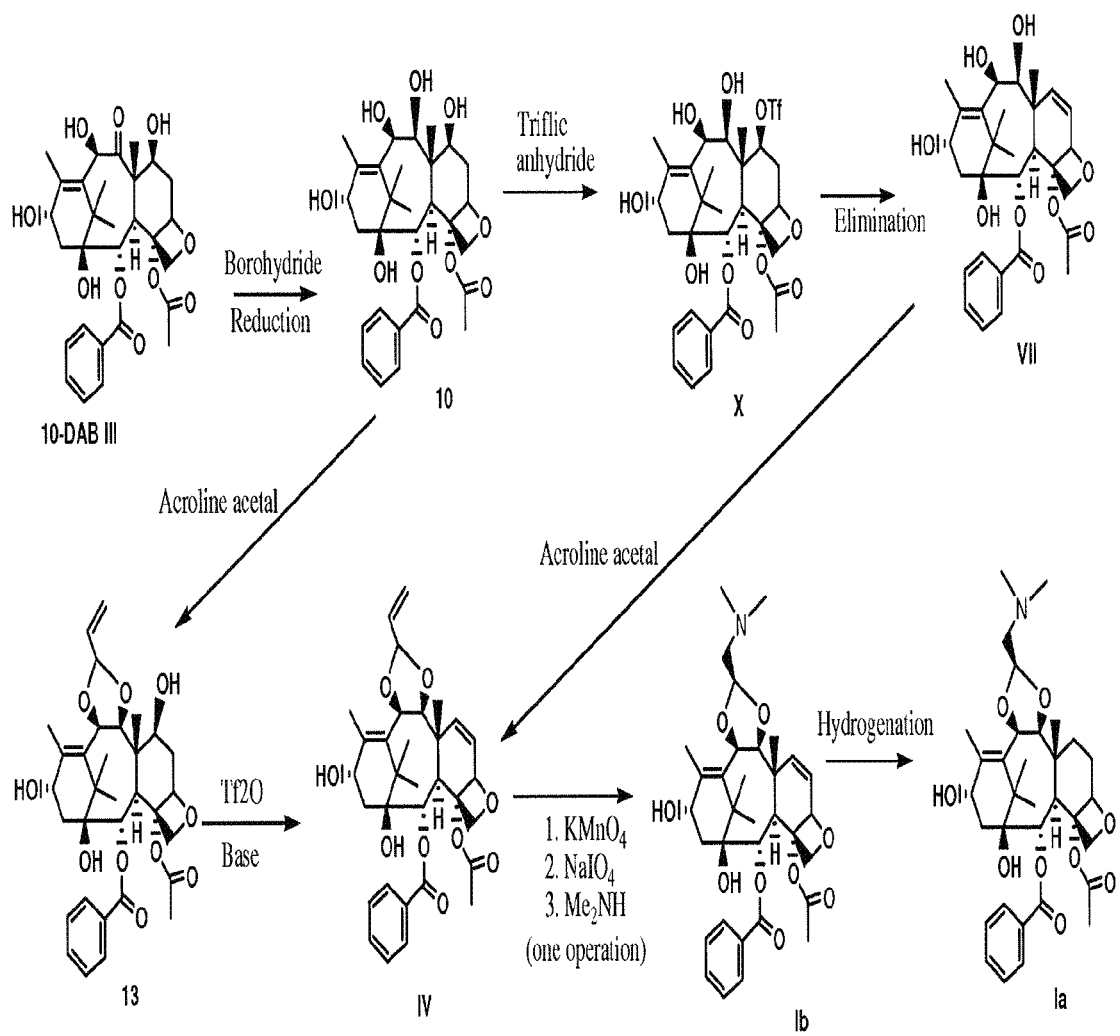
FIG. 4 is an illustration of an alternative specific reaction scheme for synthesis of the compound represented by formula (Ia).

Yet another alternative approach to synthesis of the compound represented by formula (Ia) is illustrated in FIG. 4. This synthesis also eliminates formation of the C10 formyl ester shown in FIG. 1. In a first embodiment, the compound represented by formula (Ia) is derived from the compound represented by formula (Ib), which is derived from the compound' represented by formula (IV), in a reaction scheme with early formation of the cyclic acetal. This first reaction scheme is shown in FIG. 4 as follows, starting with 10-DAB III:

Step 1: Reduction of the C9 ketone of 10-DAB III, producing a triol compound (formula 10) having hydroxyls at C9 and C10 (e.g., using borohydride);

Step 2: Formation of a C9-C10 cyclic acetal from the triol compound (formula 10), wherein the cyclic acetal is attached to a terminal olefin group. (acroline acetal and acid catalyst (e.g., camphor sulfonic acid, TFA or TSA) or Lewis acid (e.g., anhydrous zinc chloride)); and Step 3: Triflic anhydride reaction of the C7 hydroxyl (e.g., Tf₂O/Pyridine/CH₂Cl₂), followed by base elimination to form a C6-C7 double bond, producing the compound represented by formula (IV);

Step 4: Oxidatively cleaving the terminal olefin group of the cyclic acetal to an aldehyde, and reductively aminating the aldehyde to produce the compound represented by formula (Ib). (a. conversion of olefin to diol, e.g., KMnO₄ or OSO₄, b. oxidative cleavage of diol to aldehyde, e.g., periodate, e.g., NaIO₄, c. conversion of aldehyde to a dimethylaminomethyl group, e.g., Me₂NH/AcONa/NaBH(OAc)₃). These reactions can be accomplished in a single operation without purification of any intermediates to produce the compound represented by formula (Ib);

Step 5: Hydrogenation of the C6-C7 double bond of the compound represented by formula (Ib) to produce the compound represented by formula (Ia). (e.g., Rh—Al₂O₃/H₂ or Pd—C/H₂ or Pd—C/HCOONH₄)

In an alternative embodiment shown in FIG. 4 to obtain the compound represented by formula (IV), and subsequently the compound represented by formula (Ia), the compound represented by formula (IV) is derived from the compound represented by formula (VII), which is derived from the compound represented by formula (X). That is, as further illustrated in FIG. 4, the triol compound 10 obtained by reduction of the C9 ketone in Step 1 may be further reacted as follows:

Step 6: Triflic anhydride reaction of the C7 hydroxyl of the triol compound 10 to produce the compound represented by formula (X). (e.g., Tf₂O/Pyridine/CH₂Cl₂);

Step 7: Base elimination to form a C6-C7 double bond in the compound represented by formula (X), producing the compound represented by formula (VII);

Step 8: Formation of a C9-C10 cyclic acetal attached to a terminal olefin group, producing the compound represented by formula (IV). (acroline acetal and acid catalyst (e.g., camphor sulfonic acid, TFA or TSA) or Lewis acid (e.g., anhydrous zinc chloride)); and Performing Step 4 and Step 5 of the first embodiment of the FIG. 4 reaction scheme as described above to obtain the compound represented by formula (Ia).

The compound represented by formula (Ia), produced by any of the foregoing methods, can then be coupled at the C13 hydroxyl position to a taxane side chain precursor compound using any appropriate method known in the art. For example, a side chain precursor compound according to formula (II) can be coupled to the compound represented by formula (Ia) to produce a variety of pentacyclic taxane final products A specific example of such coupling using a β-lactam side chain precursor to obtain tesetaxel is illustrated in FIG. 3, wherein a protected β-lactam precursor (+)-THA is converted to (+)-TBA) (Step 9), coupled to the C13 hydroxyl group of the pentacyclic taxane core compound represented by formula (Ia) using a hindered soluble alkaline metal base, e.g., LHMDS (Step) 10, and the protecting group of the side chain of the coupled product is deprotected (Step 11) using e.g., TBAF. The β-lactam precursor TBA (1-(tert-butoxycarbonyl)-4-(3-fluoro-2-pyridyl)-3-triisopropylsilyloxy-2-azetidinone)), is disclosed in U.S. Pat. No. 7,126,003 B2 and in the U.S. Pat. No. 6,677,456 (Soga).

Figure 5:
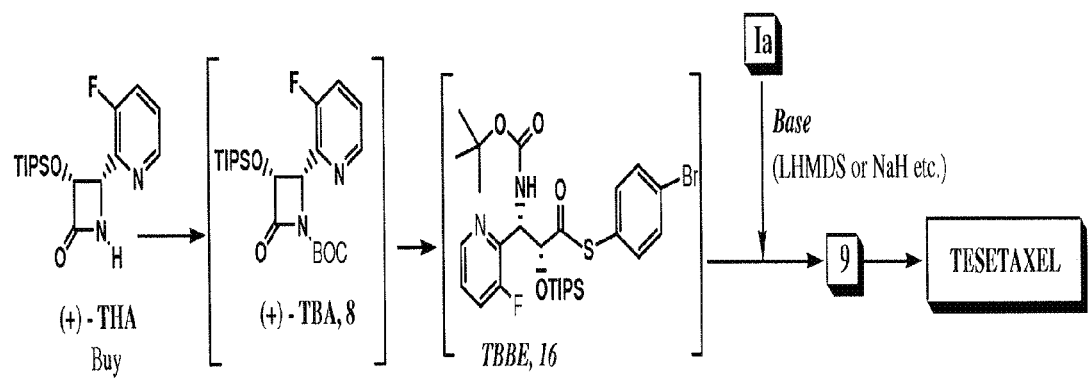
FIG. 5 is an illustration of an alternative reaction scheme for coupling the compound represented by formula (Ia) to the side chain precursor to produce tesetaxel.

Alternatively, the side chain precursor may be a functional straight chain equivalent of the β-lactam such as MBE (S-(4-Bromophenyl)(2R,3S)-3-[(tert-butoxycarbonyl)amino]-3-(3-fluoro-2-pyridinyl)-2-[(triisopropylsilyl)oxy] propanethioate), disclosed in U.S. Pat. No. 7,678,919 (Imura). The coupling reaction of the compound represented by formula (Ia) with TBBE is illustrated in FIG. 5 and discussed in more detail below.

Conventional synthesis of β-lactams for use as side chains precursors for coupling to taxane core compounds may use p-anisidine to make the acetoxyphenylazetidine (APA) intermediate, which necessitates the use of ceric ammonium nitrate (CAN) at a later step to remove the 1-phenyl substituent and convert TPA to THA. See, for example, U.S. Pat. No. 5,336,785 (Holton). This is an impractical chemistry for use on a commercial scale due to poor yield, quality issues and significant waste generation.

In an additional embodiment that addresses these problems, the invention provides a method for synthesis of the β-lactam side chain precursor for use in taxane synthesis which employs methoxy methylethoxy (MOP, or methoxydimethyl propyloxy) or other acetal groups for protection of the 3-OH of the β-lactam side chain precursor as disclosed in U.S. Pat. No. 6,310,201 (Thottathil), which is incorporated by reference herein. Although this chemistry has generally been described in U.S. Pat. No. 7,176,326 (Thottathil) and U.S. Pat. No. 6,310,201, it has not previously been applied to a β-lactam wherein the 4-substituent is heterocyclic and halogen-substituted as required for the synthesis of tesetaxel. The halogen substituent on the side chain, particularly the fluorine substitution of taxanes such as tesetaxel, is of particular interest and utility as it allows PET imaging of taxane distribution in the body, especially to cancer sites and cancer cells. The fluorinated pyridine is also particularly important for the enhanced biological activity of tesetaxel as a chemotherapeutic agent.

In this aspect the invention provides taxane side chain precursor compounds represented by formula (V) and formula (VI):

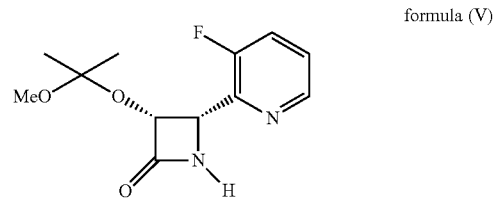

formula (V)

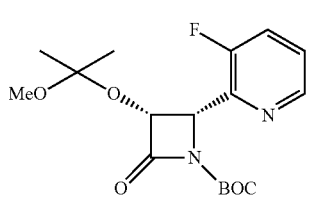

formula (VI)

wherein Me is methyl and BOC is tert, butoxycarbonyl. The compounds represented by formulas (V) and (VI) may be synthesized generally as described in U.S. Pat. No. 7,176,326 and U.S. Pat. No. 6,310,201. It will also be appreciated by those skilled in the art that other groups for protection of the 3-OH of the β-lactam side chain precursor as disclosed in U.S. Pat. No. 6,310,201 (Thottathil) may be substituted for MOP in formula (V) and formula (VI).

However, in another aspect the invention provides an alternative synthesis that avoids the use of CAN while producing a crystalline solid β-lactam side chain precursor for linkage to C13 of the taxane polycyclic core structure. The synthesis is performed according to the general reaction scheme illustrated in FIG. 2, wherein Py is pyridine or substituted pyridine; Ac is acetyl; Me is methyl; MOP is 2-methoxypropyl; and BOC is tert-butoxycarbonyl. It will also be appreciated by those skilled in the art that other groups for protection of the 3-OH of the β-lactam side chain precursor as disclosed in U.S. Pat. No. 6,310,201 (Thottathil) may be substituted for MOP in the foregoing reaction scheme. In a particular embodiment Py is a halo-substituted pyridine, such as fluoropyridine, or a methoxy-substituted pyridine. In a preferred embodiment Py is 3-fluoropyridine. When Py is 3-fluoropyridine, compound 18 of the above reaction scheme is the compound represented by formula (VI) and compound 17 is the compound represented by formula (V). Py is also intended to encompass aromatic substituents and other suitable heteroaromatic moieties.

Figure 2:
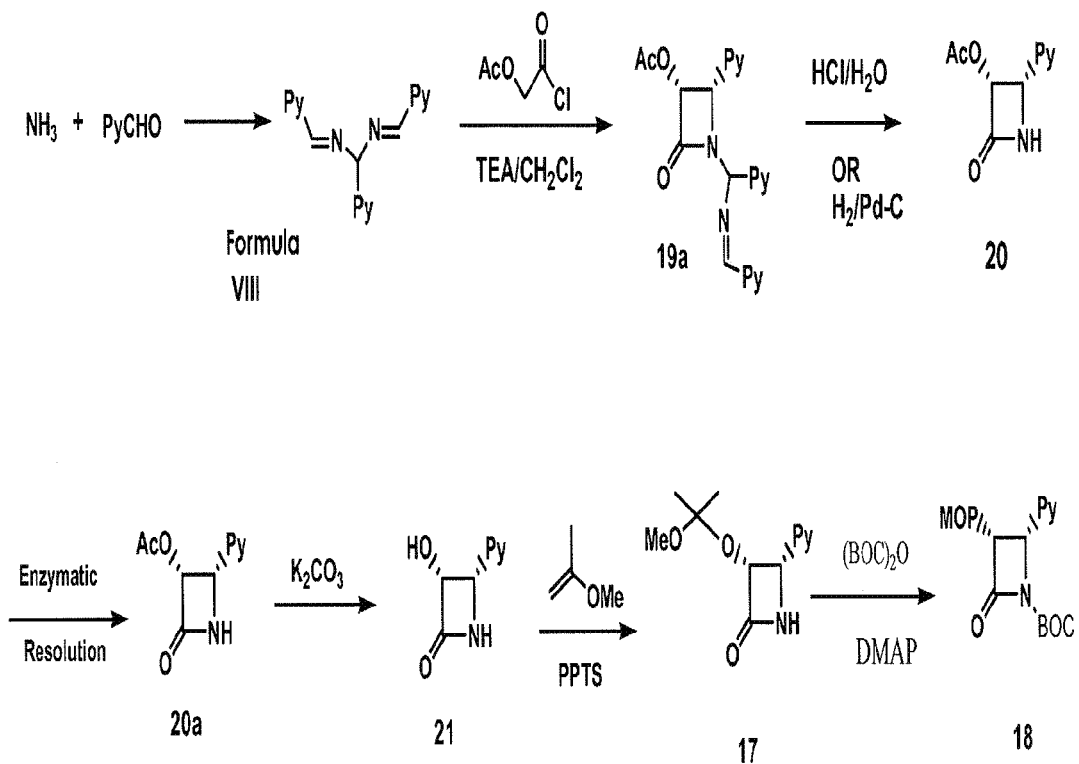
FIG. 2 is an illustration of a general reaction scheme for synthesis of a β-lactam intermediate for preparation of taxanes.

The invention also provides a compound represented by formula (VIII) which is a novel intermediate in the reaction scheme of FIG. 2 for synthesis of the compounds represented by formula (V) and formula (VI).

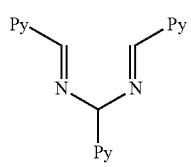

formula (VIII)

wherein Py is as defined above.

The above reaction proceeds by reacting ammonia with the aldehyde PyCHO to produce the compound represented by formula (VIII). Treatment of the compound represented by formula (VIII) with acetoxy acetyl chloride, TEA and THF forms the β-lactam ring (Compound 19a in FIG. 2) and the l-substituent is removed using a mixture of hydrochloric acid in water (hydrolysis) or a mixture of Pd—C(palladium carbon) and hydrogen (reduction) to form Compound 20. Compound 20a is formed by enzymatic resolution of Compound 20 enantiomers generally as described in U.S. Pat. No. 7,176,326. In this process Compound 20 is treated with lipase, pen-amidase or esterase and the desired enantiomer is recovered by recrystallization. Base hydrolysis of Compound 20a (for example using $K_2CO_3$) removes the acetyl to produce the 3-OH (Compound 21), which is then protected by addition of methoxypropene and pyridinium p-toluene sulfonate (PPTS), generally as described in U.S. Pat. No. 6,130,201, resulting in Compound 17. Alternatively, compound 17 is prepared by addition of methoxypropene/CSA or 2,2-dimethoxypropane/CSA. BOC is added to Compound 17 by addition of $(BOC)_2O$/DMAP to form the final product Compound 18.

In a specific embodiment for synthesis of the β-lactam side chain precursor for use in preparing tesetaxel, the aldehyde starting compound is a derivative of 3-fluoropyridine and the reaction scheme is as illustrated in FIG. 2.

For preparation of the tesetaxel side chain precursor as shown in FIG. 2, the 2-aldehyde of FFP (3-fluoropyridine) is reacted with ammonia (Step 1). Subsequent steps to prepare the compound represented by formula (VI) are as described above. In a preferred embodiment the compound represented by formula (V) is prepared using methoxypropene/CSA or 2,2-dimethoxypropane/CSA and the BOC group is added using $(BOC_2)O$/DMAP.

The compound represented by formula (VI) is coupled to the C13 hydroxyl of the compound represented by formula (Ia) to produce protected tesetaxel or another related pentacyclic taxane compound. The side chain linking reaction is preferably accomplished using a hindered soluble alkaline metal base such as lithium hexamethyl disilazide (LHMDS), which has been described in US Patent Publication 2002/0091274 (Holton), U.S. Pat. No. 6,794,523 (Holton) and U.S. Pat. No. 6,350,887 (Thottathil) for linkage of side chains to the C13 hydroxyl of 7-protected taxanes. However, other metallic bases may also be used for coupling of taxane side chains as disclosed in U.S. Pat. No. 6,350,887. Alternatively, attachment of the of the β-lactam intermediate represented by formula (VI) to the 13-position of the pentacyclic taxane intermediate represented by formula (Ia) can be performed as described in Example 6 in U.S. Pat. No. 6,677,456.

The reaction scheme using a soluble hindered base for coupling the β-lactam side chain precursor is as follows:

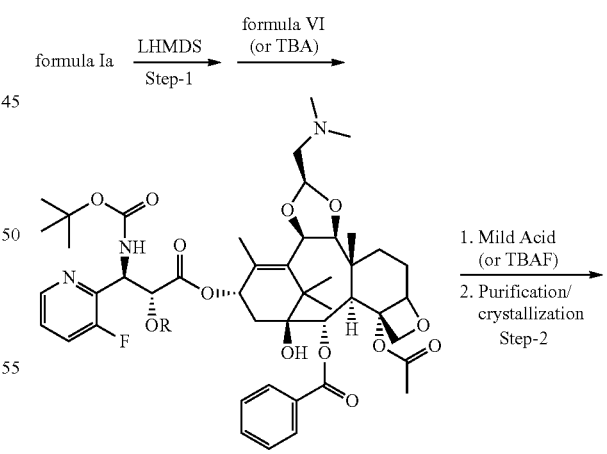

R = MOP, when formula VI is used
R = TIPS, when TBA is used
"HTX"

TESETAXEL wherein HTX refers to the intermediate compound in which the 2' hydroxyl is protected by R and R is as indicated in the reaction scheme above. The compound represented by formula (Ia) is first reacted with LHMDS or another suitable alkaline metal base in a solvent such as tetrahydrofuran (THF) as taught in Examples 7 and 9 of U.S. Pat. No. 6,677,456. Upon addition of the selected β-lactam to the reaction mixture, the 13-position OH reacts with the β-lactam to produce HTX. The 2'-OH of HTX is deprotected by treatment with mild acid or TBAF (tetrabutylammonium fluoride) generally as taught in Examples 7 and 9 in U.S. Pat. No. 6,677,456. The tesetaxel final product is purified and, optionally, crystallized to obtain the desired polymorph.

Alternatively, the β-lactam intermediate represented by formula (VI) can be converted to the functional equivalent TBBE as described below with respect to FIG. 5, and coupled to the taxane core compound represented by formula (Ia).

An example of a reaction scheme for obtaining TBBE and coupling the TBBE side chain precursor is shown in FIG. 5. As shown, TBA is synthesized by conversion of 4-(3-fluoro-2-pyridyl)-3-triisopropylsilyloxy-2-azetidinone (THA) to TBA by reaction with a butoxycarbonyl group. The 3-hydroxyl of the THA and TBA precursors can be protected by any hydroxyl protecting group, such as triisopropylsilylether (TIPS). TBBE can be derived from TBA by thio-esterification of TBA (the compound represented by formula (II)) with a thiol compound such as 4-bromothiophenol or 4-bromobenzenethiol in the presence of a base. This process is described in U.S. Pat. No. 7,678,919 (Imura). TBBE is then coupled to C13 hydroxyl group of the pentacyclic taxane core compound (e.g., the compound represented by formula (Ia)) in an inert solvent in the presence of base to produce a taxane with a hydroxyl-protected side chain. Coupling may be mediated by either bases such as sodium hydride or by soluble hindered bases such as LHMDS, and is preferably carried out in an inert gas atmosphere, such as nitrogen or argon. The coupled, protected product (9 in FIG. 3 and FIG. 5) is isolated and purified, and the side chain is deprotected to produce the final taxane compound. The final product may optionally be crystallized to obtain the desired polymorph.

One method for crystallization of tesetaxel is described in U.S. Pat. No. 7,410,980 (Uchida). This method uses acetone, a mixture of acetone and water, or a mixture of acetonitrile and water for crystallization; however, other methods for purification of tesetaxel by crystallization may be employed. Other solvents such as ethanol, methanol, isopropanol (each with or without water) may also be used for crystallization as is known in the art.

If necessary, steps may be taken to control and minimize hydrolysis of the BOC group of HTX by the acid deprotection reaction. For example, reducing the reaction temperature, shortening the reaction time and varying the reaction conditions may be employed to minimize hydrolysis of the BOC group if necessary. Alternatively, in the event of an undesirable amount of BOC hydrolysis the BOC group may simply be re-added by reaction of HTX with $Boc_2O$ in DMAP as described above.

Alternatively to coupling to the compound represented by formula (Ia) to produce 2'-O-protected tesetaxel (HTX), the compound represented by formula (II) or formula (VI) can be coupled to the C13 hydroxyl of any of the compounds represented by formula (Ib), formula (III) or formula (IV) using an alkaline metal base as described above to produce alternative intermediates in the tesetaxel synthesis schemes described above. The coupled, protected product is then deprotected and purified as described above. Coupling the side chain precursor to the alternative intermediates (represented by formula (III), formula (IV) and formula (Ib)) means that the side chain is added to the taxane core structure before completion of the tesetaxel core. These alternative intermediates may themselves be useful pentacyclic taxane compounds, but may also be reacted as described herein to complete the synthesis of the pentacyclic tesetaxel core, i.e., removal of the C6-7 double bond from the compound represented by formula (Ib); removal of one carbon from the terminal olefin of the cyclic acetal and addition of the dimethylaminomethyl substituent to the compound represented by formula (III); or removal of one carbon from the terminal olefin, addition of the dimethylaminomethyl group, and removal of the C6-7 double bond for the compound represented by formula (IV).

The final tesetaxel product may also be converted to various pharmaceutically acceptable salt forms using methods well known in the art. These salt forms will provide a variety of useful physico-chemical and pharmacological properties to tesetaxel which will be useful in different medical applications. For example, acid addition salts of tesetaxel may be prepared through dissolution thereof in an appropriate solvent in the presence of an appropriate acid prior to purification and/or crystallization. The salt forms of tesetaxel may have the general structure $(TT)_m \cdot (HX)_n$ wherein TT is tesetaxel, HX is an acid, and m and n are each independently 1 to 5.

The salts of tesetaxel and a monobasic acid may be designated TT.HX or TT.2HX. The useful monobasic acids for forming salts of tesetaxel having these structures include HCl (hydrochloric acid), HBr (hydrobromic acid), HI (hydroiodic acid), $HNO_3$ (nitric acid), HOAc (acetic acid), benzoic acid, lactic acid, MSA (methane sulphonic acid), BSA (benzene sulphonic acid), esylate (ethane sulphonic acid), sulfuric acid, CSA (camphor sulphonic acid), p-TSA (toluene sulphonic acid), mandelic acid, gentisic acid, hippuric acid, 2-hydroxyethanesulfonic acid, 2-naphthalenesulfonic acid, gluconic acid, amino acids and other pharmaceutically acceptable acids.

The salts of tesetaxel and a dibasic acid may be designated TT.HX or 2TT.HX. The useful dibasic acids for forming salts of tesetaxel having the TT.HX or 2TT.HX structure include malic acid, maleic acid, fumaric acid, oxalic acid, succinic acid, tartaric acid, malonic acid, citric acid, phosphoric acid, edisylate (1,2-ethanedisulfonate), phenyl phosphoric acid, digluconic acid, amino acids, and other pharmaceutically acceptable acids.

In a first aspect, the process of the invention for producing acid salts of tesetaxel, the selected acid in a suitable solvent is added to the reaction mixture for linking the side chain, followed by deprotection of the 2'-0 group. The final product is then subsequently purified and crystallized from the crude reaction mixture as illustrated in the following reaction scheme:

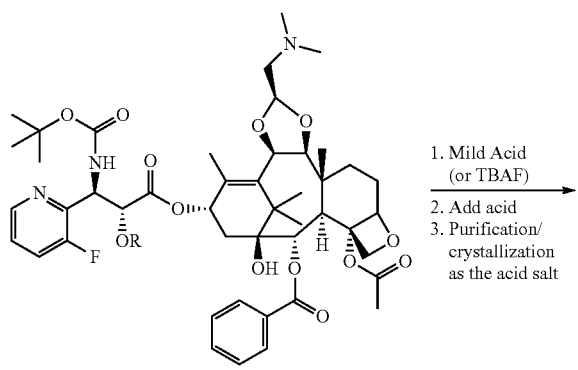

R = MOP, when formula VI is used
R = TIPS, when TBA is used
"HTX"

→ TESETAXEL Acid salt

1. Mild Acid (or TBAF)
2. Add acid
3. Purification/ crystallization as the acid salt In an alternative embodiment, the selected acid in a suitable solvent is added to the purified and isolated tesetaxel (also dissolved in a solvent) followed by crystallization of the salt form, as illustrated in the following reaction scheme:

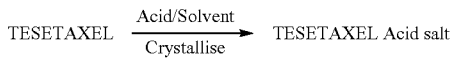

TESETAXEL →(Acid/Solvent, Crystallise)→ TESETAXEL Acid salt

EXAMPLES

Example 1

Coupling of Intermediate Compound (Ia) with the Side Chain TBA. Procedure 1

A solution of the 13-hydroxy taxane intermediate (Ia) (715 mg) in freshly dried and distilled THF was prepared and cooled to −50° C. The cooling was applied only after complete dissolution of the material. To this cooled solution was added drop wise with vigorous stirring lithium hexamethyl disilazide (LHMDS, 1.05 eq. in THF; titrated with 1,3-diphenyl acetone p-tosylhydrazone) over a period of several minutes to keep the internal temperature around −50° C. After the addition, the reaction mixture was warmed to −30° C. and stirred at that temperature for 5 minutes. A freshly prepared solution of TBA (1.1 eq.) in THF was added drop wise to the reaction mixture over a period of several minutes. No significant exotherm was observed. The flask containing TBA was washed with a few ml of THF and the washings were transferred to the reaction mixture. The resulting solution was brought to 0° C. by replacing the cooling bath with an ice-water bath. The reaction was stirred for an additional 90 minutes. The reaction was monitored by TLC and HPLC which indicated complete conversion to 2'-TIPS tesetaxel (intermediate 9).

The reaction was quenched with pH 7 phosphate buffer followed by saturated aqueous $NaHCO_3$. It was then diluted with ethyl acetate followed by conventional extractive work-up and solvent concentration to give the coupled product in quantitative yield. The crude product was further purified by silica gel polish filtration and 1.2 g of coupled material was obtained. MS MW 1037. HPLC retention time (RT) 11.2 minutes.

Example 2

Coupling of Intermediate Compound (Ia) with the Side Chain TBA. Procedure 2

In an alternate method, the procedure was repeated using 58 mg of pure 13-hydroxy taxane core intermediate (Ia) as in Example 1. The yield of the reaction was close to 100% in 94% purity (yield 77 mg). MS MW 1037. HPLC retention time (RT) 11.2 minutes.

Example 3

Deprotection of 2'TIPS Group, Intermediate 9 to Tesetaxel

A solution of 2' TIPS tesetaxel (intermediate 9) (77 mg) in ethanol-THF (1:1) solvent (5 ml) was cooled to 0° C. using an ice-bath. To this solution pre-cooled (0° C.) 1.5 N HCl (aqueous) (1 ml) was added drop wise with vigorous stirring over a period of several minutes. The reaction was stirred for several hours until HPLC and TLC indicated complete disappearance of the starting 2'TIPS tesetaxel and the presence of tesetaxel.

The conventional extractive work-up using ethyl acetate followed by solvent evaporation gave tesetaxel in quantitative yield. Depending on the purity, the crude product may be further purified by chromatography and/or crystallization. Crude yield was 70 mg, 87% HPLC purity, HPLC RT 7.9. Chromatographic purification gave 45 mg tesetaxel in 98% purity. MS MW 882.

Example 4

Alternate Deprotection of Intermediate 9 to Tesetaxel. The TBAF Method

A solution of 2' TIPS tesetaxel (intermediate 9) (1.2 gm) in ethyl acetate (10 ml) was cooled to 0-10° C. and 1.1 equivalent of tetrabutylammonium fluoride solution was added and stirred for 0.5-3 h. Completion of the reaction was monitored by HPLC. This reaction was considered completed when the starting material was ≤0.1%. At that time, 4% sodium hydrogen carbonate and saturated saline were added, and the organic layer was separated and washed with saturated saline, then concentrated under reduced pressure at ≤50° C. The crude tesetaxel at this point can be purified either by chromatography or by crystallization or by a combination of chromatography and crystallization. The yield was 535 mg with HPLC purity of 95%. HPLC RT 7.9, MS MW 882.

Example 5

Tesetaxel Crystallization

Crude tesetaxel was dissolved in acetone, activated carbon was added, and the mixture was stirred at 15-50° C. for 0.5-2 h. Insoluble matter was filtered off with a micro filter (0.2-0.25 μm) and washed with acetone. Ultra filtered (UF) water at 40-50° C. was added, and the solution was stirred for ≥6 h. The precipitate was isolated and washed with cold 40% aqueous acetone. The precipitate was then dried under reduced pressure at ≤60° C.

For a second crystallization to increase the purity and/or to control the morphology, the crystals were dissolved in acetone at ≤50° C., water was added to effect crystallization, and the mixture was stirred at room temperature for ≥6 h. Precipitated crystals were collected by filtration and washed with 40% aqueous acetone. The product was weighed and the yield of tesetaxel was calculated. The yield from crude tesetaxel obtained from crude 2'TIPS tesetaxel can be 60-80%. HPLC RT 7.9, MS MW 882. The tesetaxel was dispensed into brown bottles.

Figure 6:
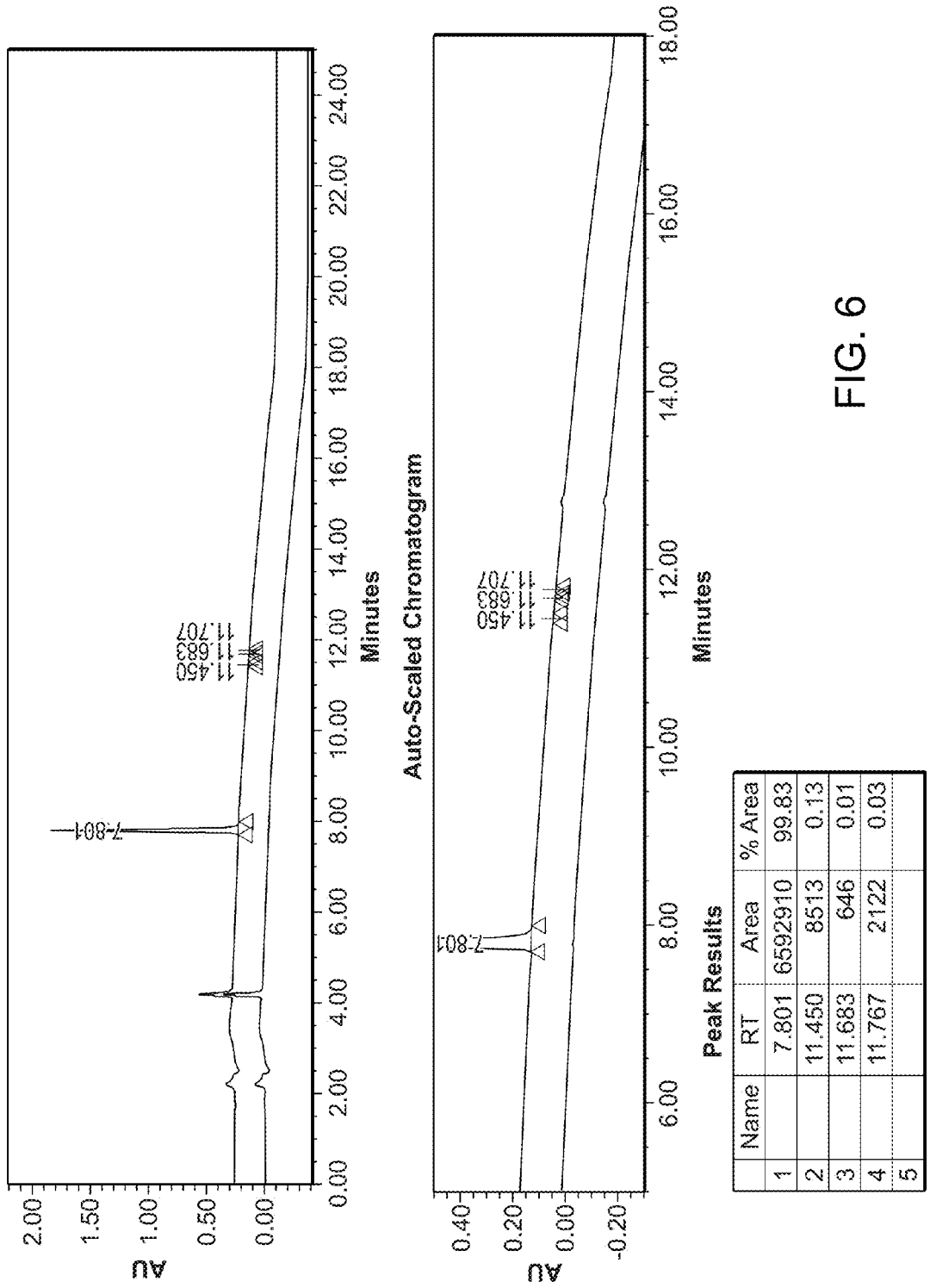
FIG. 6 is an HPLC analysis of tesetaxel produced according to the methods of the invention.

Synthesis of tesetaxel as described in Examples 1-5 was confirmed by HPLC, as shown in FIG. 6.

Example 6

Preparation of TBA 0.9 moles of (+)-THA and 10 v/w (to THA) of THF were placed in a reactor, dissolved to a solution while stirring, followed by addition of 0.0361 w/w (to THA) of DMAP and 1.0 moles of $(Boc)_2O$. The reaction was allowed to proceed at room temperature for 30 to 90 min. Completion of the reaction was checked by HPLC. Upon completion, 5 v/w of a 4% sodium bicarbonate solution was added and extraction was performed using 10 v/w (to THA) of n-hexane. The organic layer was washed with about 5 v/w tap water, and then dried over an appropriate amount of magnesium sulfate. Insoluble substances were removed by filtration and washed with about 2 v/w (to THA) of n-hexane. The filtrate, combined with the washings, was concentrated under reduced pressure at 40° C. or less to obtain TBA as a residue. HPLC Retention Time (RT) is 17.4 minutes, MS MW 439. Yield 100%. This residue was used for all tesetaxel coupling experiments.

Example 7

Preparation of TBBE

Crude TBA and 1.1 equivalent of 4-BTP (4-bromomothiophenol) were dissolved in 13 v/w of IPE (isopropyl ether), 0.3 equivalent of potassium carbonate was added, and the mixture was stirred at room temperature for 0.5 to 3 hours. Completion of the reaction was checked by HPLC.

Upon completion seven volumes of IPE and nine volumes of tap water were added and the organic layer was separated. The organic layer was washed with nine volumes of saturated saline, and then dried over an appropriate amount magnesium sulfate. Insoluble substances were removed by filtration and washed with 2 volumes of IPE. The filtrate combined with washings was concentrated under reduced pressure at 40° C. or less to obtain TBBE as a residue. Yield quantitative. HPLC purity 97%, RT 21.8 minutes. MS MW 628. This residue was used for all tesetaxel coupling experiments.

Example 8

Coupling of Intermediate Compound (Ia) with the Side Chain TBBE. Procedure 1

3.0 Equivalent of NaH and 8 volumes of DME (compared to 13-hydroxy taxane core to be used) were placed in a reactor and stirred. 0.2 to 5 g of 13-hydroxy taxane core Ia dissolved in 7 volumes of dry DME was added, followed by 1.1 equivalent of crude residue TBBE dissolved in 5 volumes of dry DME at an internal temperature of 10° C. or less. Cooling was stopped, and the reaction was allowed to proceed for 1 to 4 hours. Completion of the reaction was checked by HPLC. Upon completion, the reaction was quenched with a mixture of 9 volumes of 4% sodium bicarbonate solution and 9 volumes of ethyl acetate, and the organic layer was separated. The organic layer was washed with a mixture of 9 volumes of tap water and 6 volumes of saturated saline, and concentrated under reduced pressure at 50° C. or less. The residue obtained is 2' TIPS protected tesetaxel (compound 9).

The 2'TIPS protected tesetaxel was further purified by crystallization or chromatography and/or a combination of both chromatography and crystallization. MS MW 1037. HPLC Retention time (RT) 11.2 minutes.

The crude product obtained was also used as-is for the next deprotection step to tesetaxel.

Example 9

Alternate Coupling of Intermediate Compound (Ia) with the Side Chain TBBE. Procedure 2

The 13-hydroxy taxane core (compound Ia) (0.2 to 5 g) and 8 volumes of dry THF were placed in a reactor, cooled to −50° C. and stirred. 1.1 equivalents of LHMDS in THF (1 M) was added to the reaction and the mixture was stirred for 20 minutes at −50-30° C. 1.1 equivalents of crude residue TBBE dissolved in 5 volumes of dry THF was added and the internal temperature was raised to 0-10° C. Cooling was stopped, and the reaction was allowed to proceed for 1 to 4 hours. Completion of the reaction was checked by HPLC. Upon completion the reaction was quenched with a mixture of 9 volumes of 4% sodium bicarbonate solution and 9 volumes of ethyl acetate, and the organic layer was separated. The organic layer was washed with a mixture of 9 volumes of tap water and 6 volumes of saturated saline, and concentrated under reduced pressure at 50° C. or less. The residue obtained is 2' TIPS protected tesetaxel (compound 9).

The 2' TIPS protected tesetaxel was further purified by crystallization or chromatography and/or a combination of both chromatography and crystallization. MS MW 1037. HPLC Retention time (RT) 11.2 minutes.

The crude product obtained was also used as is for the next deprotection step to tesetaxel.

Example 10

Triflic Anhydride Reaction; Conversion of 10-DAB III to Intermediate 2 of FIG. 3

10 ml of pyridine, 2.9 g of 10-DAB III, and 2.10 g of 4-dimethylaminopyridine (DMAP) were added to the reactor. The reaction mixture was chilled and maintained under controlled temperature between 0° C. and 10° C. under nitrogen atmosphere. 1.94 g of trifluoromethansulfonic acid/anhydride was added drop wise over a period of several minutes. During the addition the reaction mixture was maintained between 0° C. and 10° C. The reaction mixture was checked by HPLC for completion. Conventional extractive work-up gave the crude product as a mixture of the triflate (intermediate 2 in FIG. 4) and the corresponding eliminated 6-7 olefin (compound IX). The crude material was used as-is for the next step. MS MW 6770. HPLC retention time (RT) 9.7 minutes.

Example 11

Alternate Procedure for 7-Hydroxy Triflation; General Protocol

A solution of 10-deacetyl baccatin (10-DAB, 1 equivalent) and pyridine (2.9 volumes, 20 equivalents) was stirred in $CH_2Cl_2$ (2 volumes) and cooled to −20° C. under nitrogen atmosphere. Trifluoromethanesulfonic anhydride ($OTf_2$) in $CH_2Cl_2$ solution (2 volumes) was added over 4 hours, keeping the internal temperature at 0° C. under nitrogen atmosphere. The resulting mixture was stirred and monitored by TLC. The reaction mixture was quenched by addition of THF (10 volumes) and HCl (1 N; 6 volumes) then the THF layer was washed with $NaHCO_3$ and NaCl saturated solutions. Evaporation of the solvent gave the crude triflate. Purification was realized by washes with DCM/MeOH 98:2.

20 g of 10-DAB gave 14 g of triflate intermediate (intermediate 2 of FIG. 3) with a chemical purity of 84% and a yield of 70%. MS MW 677. HPLC Retention time (RT) 9.7 minutes.

Example 12

Elimination of the 7-Triflate (Intermediate 2 of FIG. 3) to 6-7 Olefin (Compound IX). General Protocol A solution of 7-OTf-10DAB (intermediate 2 of FIG. 3) (1 equivalent) and DBU (5 equivalents) was stirred in THF (6.2 volumes). The resulting mixture was stirred at reflux (70° C.) for 2 h and monitored by HPLC. The reaction mixture was quenched by addition of EtOAc (10 volumes). The solution was washed with saturated $NH_4Cl$ and saturated aqueous NaCl. The organic layer was dried ($MgSO_4$), filtered and evaporated to dryness. The crude compound was purified by flash chromatography. (Merck 40-63 μm) with DCM/MeOH 98:2. 14 gm of triflate (intermediate 2 of FIG. 3) gave 9 g of desired compound (compound IX) as a white powder, after crystallization in DCM, HPLC chemical purity is 95%. The yield is 80%. MS MW 527. HPLC Retention time (RT) 4.9 minutes.

Example 13

Reduction of C6-7 Double Bond: Conversion of Compound (IX) to Intermediate XI of FIG. 3

The C6-7 olefin of compound (IX) obtained above was dissolved in 5 volumes of ethanol and 0.5 volume of water was added. 10% Pd/C 50% wet (5% wt) and ammonium formate (2×5 equivalents) was added and stirred under nitrogen atmosphere at 40 to 60° C. for 1 to 4 hours. Completion of the reaction was checked by HPLC.

Insoluble substances were removed. The residue was washed with 3 volumes of ethanol, then concentrated under reduced pressure at 50° C. or less. To the concentrated residue, 15 volumes of ethyl acetate and 3 volume of 4% sodium hydrogen carbonate and 3 volume of saturate saline were added, and the organic layer was separated. The organic layer was washed with 7 volumes of saturated saline, then dried over an appropriate amount of magnesium sulfate. Insoluble substances were removed, and the residue was washed with 3 volumes of ethyl acetate and again concentrated under reduced pressure at 50° C. or less. The crude product was purified by chromatography and/or crystallization to obtain intermediate XI.

HPLC chemical purity was 67%. The yield was 95%. MS MW 525. HPLC Retention time (RT) 10.7 minutes.

Example 14

Borane Reduction of Intermediate XI to DOH

The 9-carbonyl group of intermediate XI was reduced to the corresponding beta alcohol by the reducing agent borane-THF complex. Intermediate XI (700 mg) was dissolved in THF (10 ml) and was cooled to −10° C. under nitrogen atmosphere. 15 hydrogen equivalents of borane-THF was added drop wise and the temperature was brought to 0° C. After stirring the reaction for 2 hours, an additional amount of borane-THF (5 equivalents) was added to the reaction. After stirring the reaction for another two hours, it was quenched by adding the reaction mixture into ice-water containing 0.1% formic acid. Extractive work-up followed by chromatography gave 77% yield of the DOH product.

HPLC chemical purity was 77%. The yield was 90%. MS MW 531. HPLC retention time (RT) 10.0 minutes.

Example 15

Preparation of Acetal (Conversion Intermediate 10 to Intermediate 13 of FIG. 4)

35 L of AcOMe, 3.68 kg of alcohol intermediate 10 (FIG. 4), 0.46 kg of triethylamine HCl salt (TEA.HCl), and 2.63 kg of acrolein diethyl acetal (ADA) were added to the reactor. 14.1 g of camphorsulfonic acid (CSA) was dissolved to 1.8 L of AcOEt, the solution was added to the reaction mixture, and the temperature was kept between 15° C. and 25° C. for several hours (from 4 hours to 28 hours). The reaction mixture was checked by HPLC for completion. 37 L of isopropyl ether (IPE) was added, and 29 L of n-hexane was added. The mixture was chilled to between 10° C. and 0° C. and stirred for from 1 to 3 hours while maintaining the temperature. After stirring, the precipitate was obtained by filtration using a 60 cm Nutsche filter. The precipitate was washed with 15 L of IPE. The precipitate was then dissolved in 74 L of AcOEt. The organic layer was washed with 37 L of water followed by 18 L of water (twice). Next, 9 L of 4% $NaHCO_3$ and 9 L of saturated NaCl solution were mixed and used to wash the organic layer. The organic layer was then dried with 2 kg of $MgSO_4$. It was filtered and the residue was washed with 18 L of AcOEt. The combined organic layer was evaporated to a residue under controlled temperature between 20° C. and 40° C. 22 L of IPE was added to the residue, and the organic layer was stirred under controlled temperature between 20° C. and 30° C. 22 L of n-hexane was added to the mixture, and the mixture was stirred not less than 1 hour. After chilling under controlled temperature between 10° C. and 0° C., the mixture was stirred not less than 1 hour. The precipitate was filtered with a 60 cm Nutsche (SUS) filter and washed with 11 L of IPE. After drying with a vacuum drier, temperature controlled between 20° C. and 40° C., the crystalline form was obtained. (Standard 2.01 kg (Yield 51%), Theoretical 3.94 kg, Specification; not less than 80% by HPLC),

Example 16

Preparation of Acetal Compound (III): Procedure 1

The diol compound DOH (1 g) was dissolved in dichloromethane (10 ml) and 4 equivalents of acrolein dimethyl acetal was added to the reaction mixture. Powdered anhydrous zinc chloride (0.2 equivalents) was added and the reaction mixture was stirred at about 30° C. for 24 hours until HPLC analysis indicated complete reaction. Extractive work-up followed by chromatographic purification gave 82% yield in 96% purity. MS MW 568. HPLC Retention time (RT) 13.9

Example 17

Alternate Procedure for the Preparation of Acetal Compound (III): Procedure 2

The same procedure as that used for the conversion of intermediate 10 to intermediate 13 in Example 15 above was applied for the conversion of DOH to acetal compound (III) in 85% yield and 95% purity. MS MW 568. Retention time (RT) 13.9

Example 18

Conversion of Compound (III) to Compound (Ia)

0.17 to 7.9 g of the acetal compound III and 15 v/w of pyridine were placed in a reactor and dissolved to a solution, followed by addition of 2.5 v/w of tap water. The internal temperature was maintained between 25° C. and 55° C. 4.09 v/w of a potassium permanganate solution (50 g per liter of water) was added, and the reaction was allowed to proceed for 0.3 to 3 hours. The residual amount of acetal compound (III) was checked by HPLC. 15 v/w of ethyl acetate, 5 v/w of a 10% aqueous citric acid solution and 3 v/w of saturated saline were added, and the organic layer was separated. The organic layer was washed with a mixture of 3 v/w of a 10% aqueous citric acid solution and 3 v/w of saturated saline, followed by a wash with a mixture of 5 v/w of 4% sodium bicarbonate solution and 3 v/w of saturated saline. The washed organic layer was then concentrated under reduced pressure at 50° C. or less to obtain the diol intermediate as a residue.

The diol intermediate residue was dissolved in 7 v/w of acetonitrile, 0.15 w/w of activated carbon was added, and the mixture was stirred at 15 to 50° C. for 0.5 to 2 hours. Insoluble substances were removed, followed by addition of 3 volumes of acetonitrile and 1 v/w of pyridine, and then 3.3 v/w of tap water in which 0.426 w/w of sodium periodate was dissolved. The reaction was allowed to proceed at 15 to 50° C. for 2 hours or more. Completion of the reaction was checked by HPLC.

5 v/w of a 20% aqueous sodium thiosulfate solution was added. Insoluble substances were removed by filtration through celite and washed with 2 v/w of ethyl acetate. The filtrate combined with washings was concentrated under reduced pressure at 50° C. or less. 10 v/w of ethyl acetate and 2 volumes of saturated saline was added to the concentrated solution, and the organic layer was separated. The organic layer was washed twice with 2 v/w of saturated saline and further washed with a mixture of 4 v/w of 4% aqueous sodium bicarbonate and 4 v/w of saturated saline: The organic layer was then dried over an appropriate amount of magnesium sulfate. Insoluble substances were removed by filtration and washed with 3 v/w of ethyl acetate. The filtrate, combined with the washings, was concentrated under reduced pressure at 50° C. or less.

At a concentration of 10 v/w, 0.122 w/w of sodium acetate and 0.122 w/w of dimethylamine hydrochloride was added and stirred at 0 to 15° C. for 15 minutes to 2 hours. 0.316 w/w of sodium triacetoxyborohydride was added and stirred at 0 to 40° C. for 1 to 3 hours. Completion of the reaction was checked by HPLC.

The reaction was quenched by adding 7 v/w of a 15% aqueous potassium hydrogen carbonate solution and 3 v/w of saturated saline. The organic layer was separated and washed with 5 v/w of tap water and with 3 v/w of saturated saline, and dried with an appropriate amount of magnesium sulfate. Insoluble substances were removed by filtration and the residue was washed with 3 v/w of ethyl acetate. The filtrate was then concentrated under reduced pressure at 50° C. or less to obtain compound (Ia) as the residue. The residue was further purified by chromatography and/or crystallization.

MS MW 600. HPLC Retention time (RT) 6.2. Purity 90%

Example 19

Alternate Procedure for the Conversion of Compound (III) to Compound (Ia)

2.38 g of acetal at 0° C. and 17 volumes of pyridine/$H_2O$ were mixed, then 5.4 volumes of aqueous $KMNO_4$ (50 g/L) followed by 3.5 volumes of aqueous $KMNO_4$ (50 g/L) were added by slow addition over 30 minutes. Two peaks on HPLC (RT 9.1 and 9.3 minutes) corresponded to the two possible isomers at the newly formed hydroxyl group for this reaction. MS MW 603. Conventional extractive work-up gave crude product, 2.86 g. The crude product was used in the following step without further purification.

2.86 g of the above material at room temperature was mixed with 10 volumes acetonitrile, 1 volume of pyridine and 1.01 g of NaIO4 in 7.9 ml of water. A complete conversion was observed for the desired compound. MS MW 571. HPLC RT. 9.7. Conventional extractive work-up gave crude product, 2.2 g of material was isolated after the reaction.

For reductive amination, 1.88 g of the above crude aldehyde was dissolved at 5° C. in 24 ml of EtOAc. 290 mg of NaOAc, followed by 290 mg of $NMe_2$.HCl, followed by 752 mg of Na(AcO)3BH were added to the reaction mixture. Customary extractive work-up at the completion of the reaction gave, the crude amino compound (Ia).

Product MS MW 600. HPLC RT. 6.2. Chromatographic purification gave 1 g pure compound (Ia).

Example 20

Conversion of Compound (IV) to Compound (Ib) and then to Compound (Ia)

0.17 to 7.9 kg of the acetal compound (IV) and 15 v/w of pyridine were placed in a reactor and dissolved to a solution, and 2.5 v/w of tap water was added. The internal temperature was maintained between 25° C. and 55° C. 4.09 v/w of a potassium permanganate solution (50 g per liter of water) was added, and the reaction was allowed to proceed for 0.3 to 3 hours. The residual amount of acetal compound (IV) was checked by HPLC. 15 v/w of ethyl acetate, 5 v/w of a 10% aqueous citric acid solution and 3 v/w of saturated saline were added, and the organic layer was separated. The organic layer was washed with a mixture of 3 v/w of a 10% aqueous citric acid solution and 3 v/w of saturated saline, followed by a wash with a mixture of 5 v/w of 4% sodium bicarbonate solution and 3 v/w of saturated saline. The product was concentrated under reduced pressure at 50° C. or less to obtain the diol intermediate as a residue.

The diol intermediate residue was dissolved in 7 v/w of acetonitrile, 0.15 w/w of activated carbon was added, and the mixture was stirred at 15 to 50° C. for 0.5 to hours. Insoluble substances were removed, then 3 volumes of acetonitrile and 1 v/w of pyridine were added, followed by addition of 3.3 v/w of tap water in which 0.426 w/w of sodium periodate (compared to the amount of acetal) was dissolved. The reaction was allowed to proceed at 15 to 50° C. for 2 hours or more. Completion of the reaction was checked by HPLC.

5 v/w of a 20% aqueous sodium thiosulfate solution was added. Insoluble substances were removed by filtration through celite and washed with 2 v/w of ethyl acetate. The filtrate combined with washings was concentrated under reduced pressure at 50° C. or less. To the concentrated solution was added 10 v/w of ethyl acetate and 2 v/w of saturated saline. The organic layer was separated and washed twice with 2 v/w of saturated saline, followed by a wash with a mixture of 4 v/w of 4% aqueous sodium bicarbonate and 4 v/w of saturated saline. The organic layer was dried over an appropriate amount of magnesium sulfate, then insoluble substances were removed and washed with 3 v/w of ethyl acetate. The filtrate combined with washings was concentrated under reduced pressure at 50° C. or less. This produced the crude intermediate aldehyde.

To the above concentrate in ethyl acetate (10 v/w compared to the acetal) was added 0.122 w/w of sodium acetate and 0.122 w/w of dimethylamine hydrochloride. The mixture was stirred at 0 to 15° C. for 15 minutes to 2 hours. 0.316 w/w of sodium triacetoxyborohydride was added, and stirred at 0 to 40° C. for 1 to 3 hours. Completion of the reaction was checked by HPLC. The reaction was quenched by adding 7 v/w of a 15% aqueous potassium hydrogen carbonate solution and 3 v/w of saturated saline. The organic layer was separated, washed with 5 v/w of tap water and with 3 v/w of saturated saline, and dried with an appropriate amount of magnesium sulfate. Insoluble substances were removed, and the organic layer was washed with 3 v/w of ethyl acetate and then concentrated under reduced pressure at 50° C. or less to obtain compound (Ib) as the residue.

The residue (Ib) was dissolved in 8 v/w of ethanol (compared to acetal compound IV), 0.15 w/w of activated carbon was added, and the mixture was stirred at 15 to 50° C. for 0.5 to 2 hours. Insoluble substances were removed. 5 v/w of ethanol, 2.11 v/w of tap water, 0.5 w/w of 10% Pd/C 50% wet and 0.439 w/w of ammonium formate (compared to acetal compound IV) were added, and the mixture was stirred under nitrogen atmosphere at 40 to 60° C. for 1 to 4 hours. Completion of the reaction was checked by HPLC. Upon completion, insoluble substances were removed and washed with 3 v/w of ethanol. The reaction product was then concentrated under reduced pressure at 50° C. or less. To the concentrated residue, 15 v/w of ethyl acetate, 7 v/w of 4% sodium hydrogen carbonate and 3 v/w of saturate saline were added. The organic layer was separated and washed with 7 v/w of saturated saline, then dried over an appropriate amount of magnesium sulfate. Insoluble substances were removed and washed with 3 v/w of ethyl acetate. The reaction product was then concentrated under reduced pressure at 50° C. or less. Further purification by chromatography and/or crystallization gave compound (Ia). Product MS. MW 600. HPLC RT. 6.2. Chromatographic purification gave quality compound (Ia) in 95+% HPLC purity.

Example 21

Conversion of 10-DAB III to Intermediate 10

45 liter of AcOMe was added to the reactor (300 liter), followed by 4.5 kg of 10-DAB III and 0.65 kg of malonic acid. To this reaction mixture was added a solution of N-Bu4NBH4 in AcOMe (4.25 kg of N-Bu4NBH4 in AcOMe 23 L) (reaction temperature: 30-35° C., dropping time: 10-60 min, caution: foaming). A solution of 1.07 kg of malonic acid in 14 liter of AcOMe was slowly added to the mixture (reaction temperature: 30-35° C., dropping time: 90-150 min). After dropping, the reaction mixture was maintained at 30-35° C.

HPLC Conditions:
Sample: 0.1 ml of reaction mixture→10 ml/50% aqueous acetonitrile
Injection volume: 1 μl
Column: YMC PACK ODS-AM302 (4.6 mm*150 mm, 5 μm)
Mobile phase: 0.02M Acetate Buffer (pH 5.0)/acetonitrile (7:3)
0.02M Acetate Buffer; 1.36 g of NaOAc→500 ml, the solution was adjusted to pH 5 by AcOH solution (0.60 g of AcOH→500 ml)
Flow rate: 0.7 ml/min
Column temperature: 40° C.
Detector: UV 230 nm
Stop time: 15 min
Judgment: 10DAB III not more than 1%

5 L of water was then added to the reaction mixture, with more than 30 min of stirring. 23 L of 0.2 N HCl and 23 L of saturated NaCl solution were mixed and used for washing the reaction mixture. The extraction was done within 10 min. 23 L of 4% NaHCO$_3$ and 23 L of saturated NaCl solution were mixed and used for washing the reaction mixture. Next, 11 L of 4% NaHCO$_3$ and 11 L of saturated NaCl solution were mixed and used for washing the reaction mixture.

22.5 kg of ion exchange resin (Amberlite IRA743) was added to the organic layer. After more than 1 hour stirring, the mixture was filtered with a 60 cm Nutsche (SUS) filter. The residue was washed with 45 L of AcOEt. Combined organic layer was washed with 11 L of saturated NaCl and dried with 2 kg of MgSO$_4$. After drying, the organic layer was filtered and evaporated under controlled temperature between 20° C. and 40° C. The residue was dissolved with 2.7 liter of methanol and 9.0 liter of AcOEt, and 36 L of acetonitrile was added under controlled temperature between 20° C. and 30° C. The mixture was stirred slowly, and a precipitate formed. After not more than 1 hour stirring, the mixture was chilled to between 0° C. and 10° C. After 3 hours, the precipitate was filtered with a 60 cm Nutsche (SUS) filter. The precipitate was washed with 9 L of acetonitrile and dried at a controlled temperature between 20° C. and 40° C., producing crystalline intermediate 10. (Standard 3.68 kg (Yield 81.5%), Theoretical 4.52 kg, Specification; not less than 70% by HPLC).

HPLC Condition:
Sample: 10 mg of sample→10 ml/50% aq. acetonitrile
Injection volume: 1 μl
Column: YMC PACK ODS-AM302 (4.6 mm*150 mm, 5 μm)

Mobile phase: 0.02 M Acetate Buffer (pH 5.0)/acetonitrile (7:3) 0.02M Acetate Buffer; 1.36 g of NaOAc→500 ml, the solution was adjusted to pH 5 by AcOH solution (0.60 g of AcOH→500 ml)
Flow rate: 0.7 ml/min
Column temperature: 40° C.
Detector: UV 230 nm
Stop time: 15 min Example 22

Conversion of Compound 10 to Intermediate (X) and then to Intermediate (VII)

10 L of pyridine, 2.91 kg of compound 10 and 2.10 kg of 4-dimethylaminopyridine (DMAP) was added to the reactor. The reaction mixture was chilled to between 10° C. 0° C. under nitrogen atmosphere, and 1.94 kg of trifluoromethansulfonic acid/anhydride was dropped for between 1 hour and 3 hour. During dropping the reaction mixture was maintained at a temperature between 0° C. and 10° C. The reaction mixture was monitored by HPLC. After completion of the reaction, 14 L of cyclopentylmethyleter (CPME) was added to the mixture during stirring. The precipitate (TFA-DMAP salt) was removed by filtration using a 30 cm Nutsche filter, and washed with 16 L of CPME. The combined organic layer was first washed with 20 L of water and with 20 L of 5% aqueous NaCl solution (twice), followed by washing with 20 L of 4% NaHCO$_3$. 10 L of 4% NaHCO$_3$ and 10 L of saturated NaCl solution were mixed, and the organic layer was washed with this solution. After washing, 2 kg of MgSO$_4$, 6.0 kg of SiO$_2$ (florisil), and 4.0 kg of alumina were added to the organic layer. After drying and de-coloring, the organic layer was recovered by filtration. The precipitate was washed with 20 L of CPME. Combined organic layer was evaporated under controlled temperatures between 20° C. and 40° C. The obtained residue was dissolved in 8.0 L of chloroform and heated to a maximum temperature of 55° C. If the residue did not dissolve completely, several additional amounts of chloroform were added (up to 5 v/v volume). After slowly chilling to between 30° C. to 20° C., 16 L of IPE and 16 L of n-hexane were added. After 1 hour stirring at a temperature between 20° C. and 30° C. the precipitate was recovered by filtration with a 60 cm Nutsche (SUS) filter. The precipitate was washed with 6 L of IPE/hexane (1:1) solution. After drying with a vacuum drier at temperatures controlled between 20° C. to 40° C. for from 3 hours to 72 hours, crystalline compound VII was obtained. (Standard 1.56 kg (Yield 80.0%), Theoretical 1.95 kg, Specification; not less than 95% by HPLC).

If the product specification was not met, 4 v/v of chloroform was added to the crude product, and the solution was heated to 55° C. After heating, 8 v/v of IPE was added to the solution. After checking for precipitation, an additional 8 v/v of IPE was slowly added. After stirring for from 2 hours to 24 hours, the precipitated product compound VII was obtained by filtration. (yield 80-85%). This step can be repeated until product purity meets specifications.

Example 23

Conversion of Compound Intermediate VII to Intermediate IV

15 L of ethyl acetate, 1.8 kg of alcohol compound VII, 0.23 kg of triethylamine HCl salt (TEA.HCl), and 1.3 kg of acrolein diethyl acetal (ADA) was added to the reactor. 7 g of camphorsulfonic acid (CSA) was dissolved in 1 L of AcOEt, and the solution was added to the reaction mixture, maintaining the temperature between 15° C. and 25° C. for several hours (from 4 hours to 28 hours). The reaction mixture was checked by HPLC for completion. Upon completion, 15 L of isopropyl ether (IPE) and 15 L of n-hexane was added. The mixture was chilled to between 10° C. and 0° C., and stirred for from 1 to 3 hours while maintaining the temperature. After stirring, the precipitate was obtained by filtration using a 60 cm Nutsche filter. The precipitate (crude acetal wet) was washed with 15 L of IPE and dissolved in 30 L of AcOEt. The organic layer was washed with 15 L of water, and twice with 9 L of water. Next, 5 L of 4% NaHCO$_3$ and 5 L of saturated NaCl solution were mixed and used to wash the organic layer. The organic layer was then dried with 1 kg of MgSO$_4$. It was filtered and the residue was washed 9 liter of AcOEt.

The combined organic layer was evaporated under controlled temperature between 20° C. and 40° C. until the residue was between 1.5 w/w and 2.0 w/w. 11 L of IPE was added to the residue, and the organic layer was stirred under controlled temperature between 20° C. and 30° C. 11 L of n-hexane was added to the mixture, and the mixture was stirred for not less than 1 hour. After chilling to between 10° C. and 0° C., the mixture was stirred for not less than 1 hour. The precipitate was filtered with a 60 cm Nutsche (SUS) filter. The precipitate was washed with 5 L of IPE. After drying with vacuum drier at 20° C. and 40° C., crystalline acetal compound IV was obtained. 1.0 kg, Yield 50%.

All publications cited in the specification, both patent and non-patent publications, are indicative of the level of skill of those skilled in the art to which this invention pertains. All these publications are herein fully incorporated by reference to the same extent as if each individual publication were specifically and individually indicated as being incorporated by reference.

What is claimed is:

1. A method of making a compound, comprising coupling a taxane side chain precursor compound to a C-13 hydroxyl group of a compound of formula I

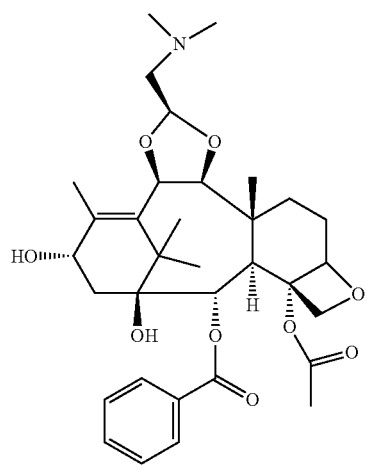

Formula (I)

to produce a protected taxane reaction product, or a salt thereof.

2. A compound having a structure of formula (II)

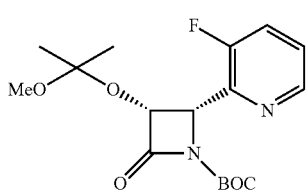

formula (II)

wherein Me is methyl and BOC is tert-butoxycarbonyl.

3. A compound having a structure of formula (III)

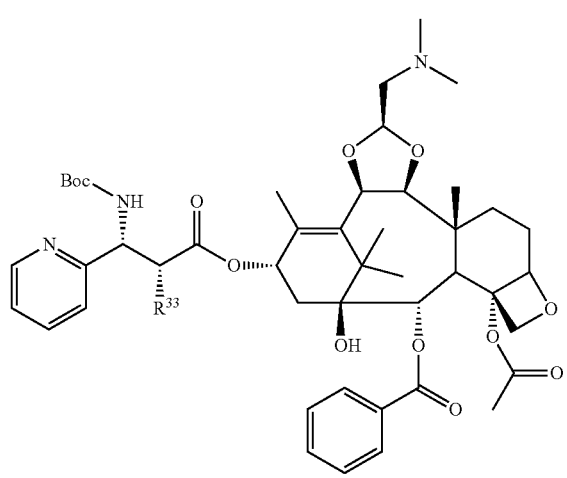

Formula (III)

wherein BOC is tert-butoxycarbonyl and $R^{33}$ is a protected hydroxyl group.

4. A method of synthesizing the compound of claim 3, comprising coupling a taxane side chain precursor compound having a formula

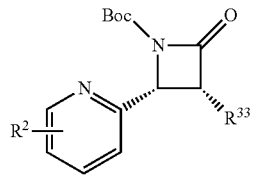

wherein $R^2$ is an alkoxy group having from 1 to 6 carbon atoms or a halogen atom and $R^{33}$ is a protected hydroxyl group to a C13 hydroxyl group of a compound having a structure of formula (I)

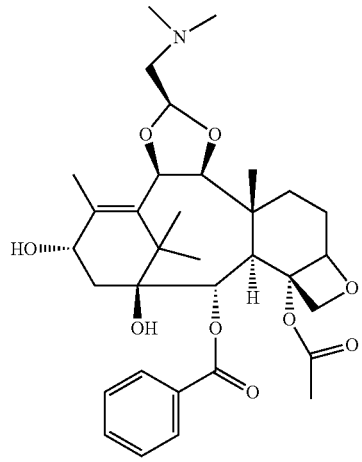

Formula (I)

to produce a protected taxane reaction product having a structure of formula (III).

5. The method of claim 4, wherein the C13 hydroxyl group is protected by a triisopropylsilyl (TIPS) or 2-methoxy propyl (MOP) group.

6. The method of claim 5, wherein $R^2$ is fluorine.

7. The method of claim 6, wherein fluorine is at the 3-position of pyridine.

8. The method of claim 4, wherein the side chain precursor compound has a formula

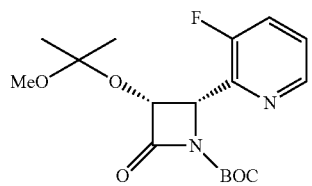

wherein Me is methyl and BOC is tert-butoxycarbonyl.

9. A method of functionalizing a vinyl acetal, comprising: providing a compound having a structure of the formula

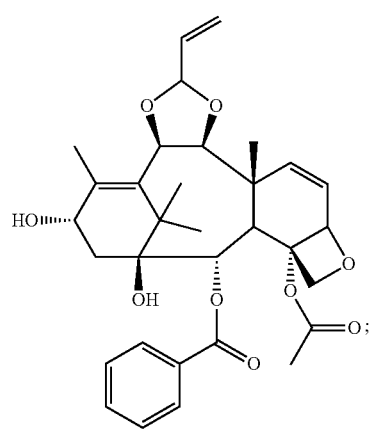

and oxidatively cleaving the terminal olefin group to form an aldehyde having the formula

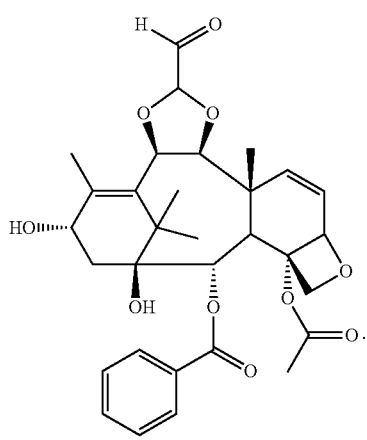

10. The method of claim 9, further comprising reductively aminating the aldehyde to provide a compound having the formula

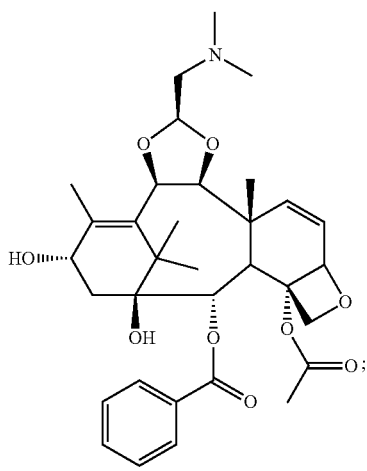

and hydrogenating the C6-C7 double bond.

11. A method of functionalizing a vinyl acetal, comprising:
providing a compound having the formula

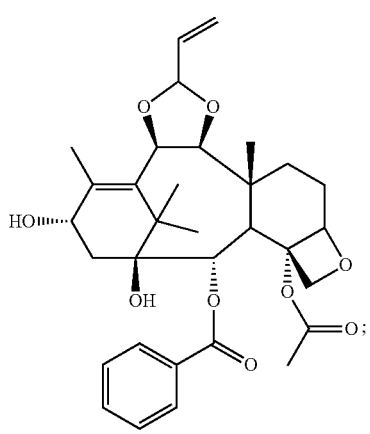

and oxidatively cleaving the terminal olefin group to form an aldehyde having a structure of the formula

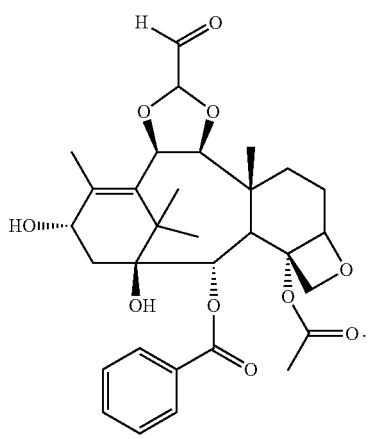

12. The method of claim 11, further comprising reductively aminating the aldehyde.

* * * * *